US008545812B2

(12) United States Patent
Hong et al.

(10) Patent No.: US 8,545,812 B2
(45) Date of Patent: Oct. 1, 2013

(54) TRANSPORT AGENTS FOR CROSSING THE BLOOD-BRAIN BARRIER AND INTO BRAIN CANCER CELLS AND METHODS OF USE THEREOF

(75) Inventors: Chang Soo Hong, Chicago, IL (US); Tohru Yamada, Oak Park, IL (US); Arsenio M. Fialho, Lisbon (PT); Tapas K. Das Gupta, River Forest, IL (US); Ananda M. Chakrabarty, Villa Park, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/481,018

(22) Filed: May 25, 2012

(65) Prior Publication Data

US 2013/0004431 A1  Jan. 3, 2013

Related U.S. Application Data

(60) Continuation of application No. 12/897,298, filed on Oct. 4, 2010, now Pat. No. 8,188,251, which is a division of application No. 11/488,695, filed on Jul. 19, 2006, now Pat. No. 7,807,183, which is a continuation-in-part of application No. 11/244,105, filed on Oct. 6, 2005, now Pat. No. 7,691,383.

(60) Provisional application No. 60/818,510, filed on Jul. 6, 2006, provisional application No. 60/700,297, filed on Jul. 19, 2005, provisional application No. 60/680,500, filed on May 13, 2005, provisional application No. 60/616,782, filed on Oct. 7, 2004.

(51) Int. Cl.
*A61K 49/00* (2006.01)
*A61K 39/00* (2006.01)
*A61K 39/095* (2006.01)

(52) U.S. Cl.
USPC ....... 424/9.2; 424/9.1; 424/184.1; 424/185.1; 424/192.1; 424/234.1; 424/249.1; 530/300; 530/350; 536/23.1; 536/23.7

(58) Field of Classification Search
USPC .................. 424/9.1, 9.2, 184.1, 185.1, 192.1, 424/234.1, 249.1; 530/300, 350; 536/23.1, 536/23.7
See application file for complete search history.

(56) References Cited

U.S. PATENT DOCUMENTS

| | | | |
|---|---|---|---|
| 5,681,810 | A | 10/1997 | Villemez et al. |
| 5,972,899 | A | 10/1999 | Zychilinsky et al. |
| 7,301,010 | B2 | 11/2007 | Chakrabarty et al. |
| 7,338,766 | B2 | 3/2008 | Chakrabarty et al. |
| 2002/0110872 | A1 | 8/2002 | Chakrabarty et al. |
| 2002/0164703 | A1 | 11/2002 | Pawlowski et al. |
| 2005/0037341 | A1 | 2/2005 | Dierynck et al. |
| 2006/0149037 | A1 | 7/2006 | Chakrabarty et al. |

FOREIGN PATENT DOCUMENTS

| | | |
|---|---|---|
| WO | 0044888 | 8/2000 |
| WO | 02070703 | 9/2002 |
| WO | 02076380 | 10/2002 |
| WO | 02079243 | 10/2002 |
| WO | 03097085 A1 | 11/2003 |
| WO | 2004046177 | 6/2004 |
| WO | 2005018662 A2 | 3/2005 |
| WO | 2006088508 | 8/2006 |
| WO | 2006-127514 A2 | 11/2006 |
| WO | 2006127477 A2 | 11/2006 |
| WO | 2007018671 A2 | 2/2007 |
| WO | 2008033820 A2 | 3/2008 |
| WO | 2008033987 A2 | 3/2008 |
| WO | 2008098216 A2 | 8/2008 |

OTHER PUBLICATIONS

Paglia et al., Cancer Immunol. Immunother., 46:88-92 (1995).
Hunter et al., The Journal of Immunolgy, 166:5878-5881 (2001).
Dang et al., Prov. Natl. Acad. Sci. USA, 98:15155-15160 (2001).
Jain, R.K and Forbes, N.S., Proc. Natl. Acad. Sci. USA, 98:4748-14750 (2001).
Vassaux et al., J. Pathology, 208:290-298 (2006).
Andersone t al., J. Molecular Biology (available online) (2005).
Hummel et al., J. Immunotherapy, 25:467-479 (2005).
Ni et al., Cancer Letter 261:1-11 (2008).
Chaudhari et al., Biochemistry, American Chemical Society 46:7 1799-1810 (2007).
Yamada et al., Cellular Microbiology 7:10 pp. 1418-1431 (2005).
Puji et al., Oncogene 23 pp. 2367-2378 (2004).
Hayashi, S et al., Journal of Bioenergetics and Biomembranes 22:3 pp. 451-471 (1990).
Xu R. et al., Database GENESCO (online). "Azurin as a bacterial protein with wide spectrum antitumor function and its use and medical composition," Abstract, 2004.
Hong CS et al., Cell Cycle 5:15 pp. 1633-1641 (2006).
Applicant's Admitted Prior Art, p. 3, Ins 19-27; pp. 9, In 16; pp. 25, Ins5-13, 2012.
Yamada et al., Infection and Immunity 70(12): pp. 7054-7062 (2002).
Anonymous: "Plastocyanin precursor" Database EMBL. Online, Nov. 1, 1997, ZP002306632 abstract.
Anonymous: "Plastocyanin precursor" Database EMBL. Online, Mar. 1, 1992, ZP002306633 abstract.
Anonymous: "Plastocyanin precursor" Database EMBL. Online, Feb. 1, 1991, ZP002306634 abstract.
Yamada et al., Cell Cycle 3(6): 752-5 (2004).
Yamada et al.; Infect. Immun. 70(12): 7054-62 (2002).
Yamada et al., Proc. Natl Acad. Sci. U.S.A 99(22):14094-103 (2002).
Zaborina et al., Microbiology 146(10): 252-30 (2000).
Apiyo, D. and Wittung-Stafshede, P., Bioche. Biophy. Res. Comm. 332:965-968 (2005).
Ye et al., Chinese Journal of Cancer 24(3):298-304 (2005).
Hiraoka et al., PNAS 101:6427-6432 (2004).
Ye et al., "Ai Zheng," 24:298-304 (2003).
Tang et al., Pharmacol. Res. 52:413-421 (2005).
Yamada et al., Cell Cycle 3:1182-1187 (2004).
Yamada et al., Cell Cycle 3:e69-e72 (2004).

(Continued)

*Primary Examiner* — Rodney P. Swartz
(74) *Attorney, Agent, or Firm* — Don J. Pelto, Esquire; Sheppard, Mullin, Richter & Hampton LLP

(57) ABSTRACT

The present invention discloses methods and materials for delivering a cargo compound into a brain cancer cell and/or across the blood-brain barrier. Delivery of the cargo compound is accomplished by the use of protein transport peptides derived from *Neisseria* outer membrane proteins, such as Laz. The invention also provides synthetic transit peptides comprised of the pentapeptide AAEAP. The invention further discloses methods for treating cancer, and specifically brain cancer, as well as other brain-related conditions. Further, the invention provides methods of imaging and diagnosing cancer, particular brain cancer.

16 Claims, 7 Drawing Sheets

(56) References Cited

OTHER PUBLICATIONS

Yamada et al., PNAS 101:4770 (2004).
Yamada et al., Cell Mircobiol 7:1418-1431 (2005).
Puji et al., J. Bacteriol. 185:3167-3178 (2003).
Chakrabarty. Microbiol. 185:2683 (2003).
Voes et al., Biochemistry, John Wiley & Sons, pp. 415-417, 932 and 933 (1990).
Definition of "necrosis" as "to make dead" according to Merriam-Webster Online dictionary downloaded from www. m-w.com on Apr. 25, 2005.
Zaborina et al., Molecular Microbiology 31(5): 33-1343 (1999).
Confer, A.W. and Durham, Janet A., Am. J. Res. 53(5):646-652 (1992).
Wu, T. et al., "Antimicrobial Agents and Chemotherapy," 44(5):1200-1208 (2000).
PCT International Application No. PCT/US02/01408—International Search Report.
PCT International Application No. PCT/US04/—International Search Report.
European Application No. EP02739075.6—Supplemental Search Report, 2012.
Kukimoto, M. et al., FEBS Letters. 394:87-9 (1996).
Cutruzzola et al., K. Inorganic Chemistry, 88:353-361 (2002).
Murphy LM et al., J. Mol. Biol., 315.859-871 (2002).
Punj, V. and Chakrabany, A.M., Cellular Microbology 5(4):225-23 (2003).
Yamada et al., PNAS, 99(22):14098-14103 (2003).
Goto et al, Mol. Bio. 47(2)549-559 (2003).
Punj et al., Biochemical and Blophysical Research Communication, 32:109-114 (2003).
Zaborina et al., Infect. Immun. 67:5231-5242.
Melnikov et al., Mol. Microbiol. 366:1481-1493 (2000).
Punj et al., Infect. Immun. 68:4937-4937 (2000).
Zaborina et al., Microbiology, 146:2521-2560 (2000).
Kim et al., The Journal of Clinical Investigation, 105(7):837-839 (2000).
Sznol et al., The Journal of Clinical Investigation, 105(8):1027-1030 (2000).
Pawelek et al., Cancer Research, 57:4537-4544 (1997).
Potera, ASM News, 66(6) (2000).
Alexandroff et al., The Lancet, 53:1689-1694 (1999).
O'Donnell, Tibech 15:512-517 (1997).

SEQUENCE LISTING

<160> NUMBER OF SEQ ID NOS: 25

<210> SEQ ID NO 1
<211> LENGTH: 1140
<212> TYPE: DNA
<213> ORGANISM: Neisseria gonorrhoeae

<400> SEQUENCE: 1

```
ctggcaggct tgacgcttcg atacgctctg tttcggtcag gctggtcccg aaaccggaaa      60
aaccgccgaa aaccaatacc ctgcatttga gtaaggctgc gctggagagt ttcggttcgg     120
cggcggcaaa gttggaaaaa cggcatcccg aattggcgga ggcattggca aacttggtta     180
gaaggcatgg cgcataaaat gtatacggga atttgtgtaa acatccgtta atattaagaa     240
gtaaaggata atgggtctaa tactaaagaa ataggttcgg ggtaaaattg cccctttttaa     300 agtaaacgat tgtaaacttg cagacaggct ttgatttcaa atgaaatttg tagcaaaatg     360
ccgccccgaa acatctgttt gtgcaacgcg gcggaatctt tttcaaggtt ttgttaatgg     420
cggttgcact ttgatttctg taaaaccgaa tattatttta tcgattggag atttaccatg     480
aaagcttatc tggctctgat ttctgccgcc gttatcggtt tggctgcctg ctctcaagaa     540
cctgccgcgc ctgctgccga ggcaactcct gctgctgaag cacccgcttc cgaagcgcct     600
gccgccgaag ctgctcctgc agatgctgcc gaagcccctg ctgccggcaa ttgtgcggca     660
actgtcgaat ccaacgacaa tatgcagttc aacaccaaag acatccaagt cagcaaagca     720
tgtaaagagt ttaccatcac tctgaaacat accggtacgc aacccaaagc cagcatgggt     780
cacaaccttg tgattgccaa agctgaagac atggacggcg tatttaaaga cggcgtaggt     840
gctgccgata ccgactatgt caaacctgac gatgcgcgcg ttgttgccca caccaaactg     900
atcggcggcg gcgaagagtc ttccctgact ctggatcctg ccaaattggc tgacggcgac     960
tacaaatttg cctgcacttt cccgggtcac ggtgctttga tgaacggcaa agtgactttg    1020
gtcgattaat ccgcttaaag tctcaaaaga cggacagcct gctttgtgca ggctgtttta    1080
ttataaaatg actgcttgaa aagtgccccg ttgagaacga aaacatgaat ccgtttgaaa    1140
```

<210> SEQ ID NO 2
<211> LENGTH: 540
<212> TYPE: DNA
<213> ORGANISM: Pseudomonas aeruginosa

<400> SEQUENCE: 2

```
cttttcatg cagcggatcg ctcgcgcatc acttcagggt cagggtgccc ttcatcagcg      60
cggagtggcc cggaaggtg cagaagaaca tgtactgctc gccttccttc agcttggaga     120
cgtcgaaggt caccgagtcc ttctcgcccg agccgatcag cttggtgtgg gcgatgacac     180
```

```
ggctgtcgtc gggcttcagg taatccttgt ccaggccgga agccatgccg tcggtgacca      240
cgccctgcat gtcggcggcg gtgctcagta cccagttgtg gcccatgacg ttcttcggca      300
ggttgccggg gtgggacagg ttgacggtga actgcttgca gctcttgtcg acggtgatgg      360
cattggtgtt gaactgcatc tggtcgttac cctggatgtc caccgagcac tcggcagcca      420
gcagtggcgc actgagcagg acagcaggg ataccgcagc gagtttacgt agcatggagc       480
agcctcctag gcaggttggg cgatgaatcc tgaaagagca gactgcccga tcgggcaccg      540

<210> SEQ ID NO 3
<211> LENGTH: 117
<212> TYPE: DNA
<213> ORGANISM: Neisseria gonorrhoeae

<400> SEQUENCE: 3
tgctctcaag aacctgccgc gcctgctgcc gaggcaactc ctgccggtga agcacccgct       60
tccgaagcgc ctgccgccga agctgctcct gcagatgctg ccgaagcccc tgctgcc         117

<210> SEQ ID NO 4
<211> LENGTH: 33
<212> TYPE: DNA
<213> ORGANISM: artificial sequence
<220> FEATURE:
<223> OTHER INFORMATION: forward primer for Laz

<400> SEQUENCE: 4
ccggaattcc ggcagggatg ttgtaaatat ccg                                    33

<210> SEQ ID NO 5
<211> LENGTH: 38
<212> TYPE: DNA
<213> ORGANISM: artificial sequence
<220> FEATURE:
<223> OTHER INFORMATION: PCR primer

<400> SEQUENCE: 5
ggggtaccgc cgtggcaggc atacagcatt tcaatcgg                               38

<210> SEQ ID NO 6
<211> LENGTH: 27
<212> TYPE: DNA
<213> ORGANISM: artificial sequence
<220> FEATURE:
<223> OTHER INFORMATION: PCR primer

<400> SEQUENCE: 6
ggcagcaggg gcttcggcag catctgc                                           27

<210> SEQ ID NO 7
<211> LENGTH: 26
<212> TYPE: DNA
<213> ORGANISM: artificial sequence
<220> FEATURE:
<223> OTHER INFORMATION: PCR primer

<400> SEQUENCE: 7
ctgcaggtcg actctagagg atcccg                                            26

<210> SEQ ID NO 8
<211> LENGTH: 25
<212> TYPE: DNA
<213> ORGANISM: artificial sequence
<220> FEATURE:
<223> OTHER INFORMATION: PCR primer
```

```
<400> SEQUENCE: 8
gccgagtgct cggtggacat ccagg                                       25

<210> SEQ ID NO 9
<211> LENGTH: 27
<212> TYPE: DNA
<213> ORGANISM: artificial sequence
<220> FEATURE:
<223> OTHER INFORMATION: PCR primer

<400> SEQUENCE: 9
tactcgagtc acttcagggt cagggtg                                     27

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
cttcagggtc agggtgccct tcatc                                       25

<210> SEQ ID NO 11
<211> LENGTH: 26
<212> TYPE: DNA
<213> ORGANISM: artificial sequence
<220> FEATURE:
<223> OTHER INFORMATION: primer

<400> SEQUENCE: 11
ctgcaggtcg actctagagg atcccg                                      26

<210> SEQ ID NO 12
<211> LENGTH: 26
<212> TYPE: DNA
<213> ORGANISM: artificial sequence
<220> FEATURE:
<223> OTHER INFORMATION: primer

<400> SEQUENCE: 12
tgctctcaag aacctgccgc gcctgc                                      26

<210> SEQ ID NO 13
<211> LENGTH: 38
<212> TYPE: DNA
<213> ORGANISM: artificial sequence
<220> FEATURE:
<223> OTHER INFORMATION: primer

<400> SEQUENCE: 13
taggatcctt aggcagcagg ggcttcggca gcatctgc                         38

<210> SEQ ID NO 14
<211> LENGTH: 31
<212> TYPE: DNA
<213> ORGANISM: artificial sequence
<220> FEATURE:
<223> OTHER INFORMATION: primer

<400> SEQUENCE: 14
cgagctcatg tccctatac taggttattg g                                 31

<210> SEQ ID NO 15
<211> LENGTH: 40
```

```
<212> TYPE: DNA
<213> ORGANISM: Artificial sequence
<220> FEATURE:
<223> OTHER INFORMATION: primer

<400> SEQUENCE: 15
cccaagcttt caggggatcc cacgaccttc gatcagatcc                            40

<210> SEQ ID NO 16
<211> LENGTH: 26
<212> TYPE: DNA
<213> ORGANISM: artificial sequence
<220> FEATURE:
<223> OTHER INFORMATION: primer

<400> SEQUENCE: 16
ggaattcata tgaaagctta tctggc                                          26

<210> SEQ ID NO 17
<211> LENGTH: 27
<212> TYPE: DNA
<213> ORGANISM: artificial sequence
<220> FEATURE:
<223> OTHER INFORMATION: primer

<400> SEQUENCE: 17
ccggaattcg gcagcagggg cttcggc                                         27

<210> SEQ ID NO 18
<211> LENGTH: 33
<212> TYPE: DNA
<213> ORGANISM: artificial sequence
<220> FEATURE:
<223> OTHER INFORMATION: primer

<400> SEQUENCE: 18
cgggatcccc tgctctcaag aacctgccgc gcc                                  33

<210> SEQ ID NO 19
<211> LENGTH: 41
<212> TYPE: DNA
<213> ORGANISM: artificial sequence
<220> FEATURE:
<223> OTHER INFORMATION: primer

<400> SEQUENCE: 19
cggaattctt aggcagcagg ggcttcggca gcatctgcag g                         41

<210> SEQ ID NO 20
<211> LENGTH: 31
<212> TYPE: DNA
<213> ORGANISM: artificial sequence
<220> FEATURE:
<223> OTHER INFORMATION: primer

<400> SEQUENCE: 20
cgagctcatg tcccctatac taggttattg g                                    31

<210> SEQ ID NO 21
<211> LENGTH: 32
<212> TYPE: DNA
<213> ORGANISM: artificial sequence
<220> FEATURE:
<223> OTHER INFORMATION: primer

<400> SEQUENCE: 21
ccgctcgagt caggcagcag gggcttcggc ag                                   32
```

```
<210> SEQ ID NO 22
<211> LENGTH: 166
<212> TYPE: PRT
<213> ORGANISM: Neisseria gonorrhoeae

<400> SEQUENCE: 22

Cys Ser Gln Glu Pro Ala Ala Pro Ala Ala Glu Ala Thr Pro Ala Gly
1               5                   10                  15

Glu Ala Pro Ala Ser Glu Ala Pro Ala Ala Glu Ala Ala Pro Ala Asp
            20                  25                  30

Ala Ala Glu Ala Pro Ala Ala Gly Asn Cys Ala Ala Thr Val Glu Ser
        35                  40                  45

Asn Asp Asn Met Gln Phe Asn Thr Lys Asp Ile Gln Val Ser Lys Ala
    50                  55                  60

Cys Lys Glu Phe Thr Ile Thr Leu Lys His Thr Gly Thr Gln Pro Lys
65                  70                  75                  80

Ala Ser Met Gly His Asn Leu Val Ile Ala Lys Ala Glu Asp Met Asp
                85                  90                  95

Gly Val Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
        115                 120                 125

Glu Glu Ser Ser Leu Thr Leu Asp Pro Ala Lys Leu Ala Asp Gly Asp
    130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 23
<211> LENGTH: 128
<212> TYPE: PRT
<213> ORGANISM: Pseudomonas aeruginosa

<400> SEQUENCE: 23

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 24
<211> LENGTH: 39
<212> TYPE: PRT
<213> ORGANISM: Neisseria gonorrhoeae
```

```
<400> SEQUENCE: 24

Cys Ser Gln Glu Pro Ala Ala Pro Ala Ala Glu Ala Thr Pro Ala Gly
1               5                   10                  15

Glu Ala Pro Ala Ser Glu Ala Pro Ala Ala Glu Ala Ala Pro Ala Asp
            20                  25                  30

Ala Ala Glu Ala Pro Ala Ala
        35

<210> SEQ ID NO 25
<211> LENGTH: 5
<212> TYPE: PRT
<213> ORGANISM: artificial sequence
<220> FEATURE:
<223> OTHER INFORMATION: repeat sequence

<400> SEQUENCE: 25

Ala Ala Glu Ala Pro
1               5
```

TRANSPORT AGENTS FOR CROSSING THE BLOOD-BRAIN BARRIER AND INTO BRAIN CANCER CELLS AND METHODS OF USE THEREOF

RELATED APPLICATIONS

This application claims priority under 35 U.S.C. §§119 and 120 to and is a continuation of U.S. patent application Ser. No. 12/897,298, filed on Oct. 4, 2010 and issued as U.S. Pat. No. 8,188,251 on May 29, 2012, which is a division of U.S. patent application Ser. No. 11/488,695, filed on Jul. 19, 2006 and issued as U.S. Pat. No. 7,807,183 on Oct. 5, 2010, which claims priority to U.S. Provisional Patent Application No. 60/818,510, filed Jul. 6, 2006, and U.S. Provisional Patent Application No. 60/700,297, filed on Jul. 19, 2005, and which is a continuation-in-part of U.S. patent application No. 11/244,105, filed on Oct. 6, 2005 and issued as U.S. Pat. No. 7,691,383 on Apr. 6, 2010, which claims priority to U.S. Provisional Patent Application No. 60/616,782, filed on Oct. 7, 2004, and U.S. Provisional Application No. 60/680,500, filed on May 13, 2005, and U.S. Provisional Application No. 60/700,297, filed on Jul. 19, 2005. The entire content of these applications is fully incorporated herein by reference.

STATEMENT OF GOVERNMENTAL INTEREST

The subject matter of this application has been supported by a research grant from the National Institutes of Health (NIH), Bethesda, Md., U.S.A., (Grant Number ES 04050-18). The government has certain rights in the invention.

BACKGROUND

The development of new drugs for the brain has progressed at a much slower pace than that for the rest of the body. This slow progress has been due in large part to the inability of most drugs to cross the brain capillary wall, which forms the blood-brain barrier (BBB), to enter the brain. Approximately 100% of large-molecule drugs, and greater than 98% of small-molecule drugs do not cross the BBB. Only a small class of drugs, small molecules with a high lipid solubility and a molecular mass of less than 400-500 daltons actually cross the BBB. And of the small molecules that cross the BBB, only a small percentage cross the BBB in a pharmaceutically significant amount. (Pardridge, Molecular Innovations 3:90-103 (2003))

Only a few diseases of the brain respond to the small molecule drugs that can cross the BBB, such as depression, affective disorders, chronic pain and epilepsy. Far more diseases of the brain do not respond to the convention lipid-soluble small molecular mass drugs, such as Alzheimer disease, stroke/neuroprotection, brain and spinal cord injury, brain cancer, HIV infection of the brain, various ataxia-producing disorders, amyotrophic lateral sclerosis (ALS), Huntington disease, childhood inborn genetic errors affecting the brain, Parkinson's disease and multiple sclerosis. Even the few diseases of the brain for which effective small molecule drugs are available require further research and the development of new and improved drugs. Id.

Particularly difficult to treat are cancers of the brain. The common forms of cancer in the brain are glioblastoma multiforme (GBM) and anaplastic astrocytoma (AA). The mean survival for patients with GBM is approximately 10 to 12 months, while the median survival for patients with AA is 3 to 4 years. For patients with GBM, surgery will prolong their lives only a few months. (Kufe et al., *Cancer Medicine*, §§23 and 83, ($6^{th}$ ed. BC Decker, 2003)) Most cases where treatment of GBM is by surgery and local irradiation result in relapse within 2 to 4 cm of the original tumor margins. Id.

Current approaches to administer a drug that doesn't cross the BBB into the brain include by craniotomy, a process by which a hole is drilled in the head and the drug administered by either intracerebroventricular (ICV) or intracerebral (IC) injection. With IC administration, the drug remains at the site of deposit at the tip of the needle. With ICV administration, the drug distributes only as far as the ependymal surface of the ipsilateral ventricle and does not penetrate significantly into the brain parenchyma. Therefore, the IVC and IC administration methods reach less than 1% of the brain volume, and there are few diseases of the brain that can be treated by such limited penetration. Id.

In contrast, a transvascular route of drug delivery could treat virtually 100% of the neurons of the brain. Because every neuron is perfused by its own blood vessel, a drug administered tranvascularly can reach every neuron of the brain after crossing the BBB. However, because there is no drug-targeting system that will allow drugs to cross the BBB, the transvascular route of administration is unavailable to the vast majority of drug candidates.

In spite of the fact that most drugs and other molecules cannot cross the BBB, certain bacterial and fungal/viral pathogens are known to cross the BBB to cause infection. (Nassif, et al., Trends Microbiol. 10:227-232 (2002)) Such bacterial pathogens could be either extracellular such as *Neisseria meningitidis, Streptococcus pneumoniae* and *Escherichia coli* K-1, or intracellular such as *Listeria monocytogenes* or *Mycobacterium tuberculosis*. While the intracellular pathogens mostly invade the brain meninges by hiding inside infected leukocytes, the extracellular pathogens enter the central nervous system by first disseminating in the blood stream and then directly interacting with the luminal side of the cerebral endothelia, thereby disrupting the tight junctions of the brain microvascular endothelial cells. (Nassif et al., id.; Drevets & Leenen, Microbes Infect. 2:1609-1618 (2000); Kim, Subcell. Biochem. 33:47-59 (2000)) This interaction allows the pathogen to invade the brain meninges causing meningitis. Using in vitro monolayer and bilayer models for crossing the BBB as well as isolating bacterial mutants incapable of passage through such model mono- or bi-layers, a variety of bacterial proteins have been implicated in overall invasion and crossing of the BBB. (Huang & Jong, Cell. Microbiol. 3:277-287 (2001)) For example, *E. coli* K-1 genes such as ibeA, ibeB, aslA, yijP and ompA or *N. meningitidis* genes encoding proteins such as type IV pili, Opc, Opa, etc, and viral proteins such as HIV surface protein gp120, have all been suggested to allow effective invasion and crossing of the BBB to cause infection. In the case of extracellular bacterial pathogens, such proteins are believed to allow both adherence and subsequent breaching of the BBB for invasion of the meninges. (Nassif et al., id; Huang & Jong, id.) No single bacterial surface protein has been demonstrated to facilitate disruption of the tight junctions to allow crossing of the BBB.

An azurin-like gene exists in many gonococci and meningococci, such as *Neisseria gonorrhoeae* and *N. meningitidis*. (Gotschlich & Seiff, FEMS Microbiol. Lett. 43:253-255 (1987); Kawula, et al., Mol. Microbiol. 1:179-185 (1987)) Azurin is produced by a number of pathogenic bacteria and there is significant sequence homology among such genes. (Yamada, et al., Cell. Microbiol. 7:1418-1431 (2005)) A protein epitope termed "H.8" is conserved among pathogenic *Neisseria* species and is detected by the binding of a monoclonal antibody designated H.8. Two distinct gonococcal genes, laz and lip, encode proteins that cross-react with the H.8 monoclonal antibody. (Hayashi & Wu, J. Bioenerg. Biomembr. 22:451-471 (1990))

Many pathogens have azurin-like proteins, but *Neisseria* is unique in having the H.8 region attached to it. Laz and Lip are gonococcal outer surface proteins that contain a signal peptide lipoprotein consensus sequence that is recognized by the bacterial enzyme signal peptidase II, which processes the sequence to result in the N-terminal acylation of a cysteine residue with fatty acid and glycerol. (Hayashi & Wu, id.; Yamada, et al., Cell. Microbiol. 7:1418-1431 (2005)). The Lip lipoprotein, about 6.3 kDa, consists almost entirely of pentapeptide repeats of the motif Ala-Ala-Glu-Ala-Pro (AAEAP (SEQ ID NO: 25)), while the Laz lipoprotein, about 17 kDa, includes a 39 amino acid region at the N-terminus containing imperfect AAEAP (SEQ ID NO: 25) repeats. (Gotschlich & Seiff, id.; Kawula, et al., id.; Woods et al., Mol. Microbiol. 3: 43-48 (1989)). Beyond this 39 amino acid N-terminal region in Laz is a 127 amino acid region that is highly homologous to *P. aeruginosa* azurin. (Cannon, Clin. Microbiol. Rev. 2:S1-S4 (1989)) Laz is involved in defense against oxidative stress and copper toxicity and increases survival in an ex vivo primary human ectocervical epithelial assay. (Wu, et al., Infect. Immun. 73:8444-8448 (2005))

A third *N. gonorrhoeae* outer membrane protein, Pan 1, also has the AAEAP (SEQ ID NO: 25) pentapeptide repeat motif. (Hoehn and Clark, Infection and Immunity, 60: 4704-4708 (1992)) The size of Lip varies in different *Neisserial* strains. In strain FA1090, Lip is 71 amino acids in length with 13 repeats of AAEAP (SEQ ID NO: 25) and six amino acids not a part of the repeats. In strain R10, Lip is 76 amino acids in length with 14 AAEAP (SEQ ID NO: 25) repeats. (Cannon, id.) Purified Lip peptide is a potent inflammatory mediator capable of inducing the release of the chemokine interleukin-8 (IL-8) and the cytokine IL-6 by immortalized human endocervical epithelial cells, and the production of IL-8 and the activation of the transcription factor NF-kB by human embryonic kidney 293 cells transfected with toll-like receptor 2. (Fisette, et al., J. Biol. Chem. 278:46252-46260 (2003))

In light of the large number of patients world-wide with serious disorders of the brain and spinal cord, what is needed is a transport system that can take hydrophilic molecules and large molecules across the BBB. Preferably, this delivery system would have a high degree of specificity to allow drugs to be targeted to the brain without making a generally leaky BBB. Further, a successful delivery system would be generally benign and would allow repeated use of the system on the patient without undesirable side-effects. In some cases, a successful delivery system would deliver a drug to all areas of the brain equally. In other cases, the delivery system would deliver drugs specifically to brain cancer cells.

SUMMARY OF THE INVENTION

The invention provides transit peptides derived from *Neisseria* outer membrane proteins that can facilitate the transport of attached or associated cargo compounds into brain cancer cells and/or across the blood brain barrier. Also provided are complexes of the transit peptide and its cargo compound, as well methods of use of both the complexes and the transit peptides to diagnose and treat brain cancer, as well as diagnose and treat other conditions related to the brain. Finally the invention provides kits comprising the transit peptides and/or complexes, and/or nucleic acids encoding the same.

One aspect of the invention is isolated transit peptides which are a variant, derivative or structural equivalent of Laz, Lip or Pan 1 from *Neisseria*, and which facilitate the entry of a linked molecule into a mammalian brain cancer cell or across the blood-brain barrier. The H.8 region of Laz (SEQ ID NO: 24) may have at least 90% amino acid identity to these transit peptides. In some embodiments, the transit peptide is SEQ ID NO: 24. In other embodiments, the transit peptides may be modified to extend or optimize the half life of the peptide in the bloodstream.

Another aspect of the invention are transit peptides, which comprises a region of at least 4 imperfect or perfect repeats of Ala-Ala-Glu-Ala-Pro (SEQ ID NO: 25), and which region has at least about 50% AAEAP (SEQ ID NO: 25) pentapeptide repeats per total length. In some embodiments, the region of imperfect or perfect repeats is at least about 90% identical to a peptide comprising an equal number of repeats of Ala-Ala-Glu-Ala-Pro (SEQ ID NO: 25). In some embodiments, these transit peptides are synthetic. In other embodiments, these transit peptides may be modified to extend or optimize the half life of the peptide in the bloodstream.

Another aspect of the invention are complexes comprising at least one cargo compound linked to a transit peptides comprising a region consisting of at least 4 imperfect or perfect repeats of Ala-Ala-Glu-Ala-Pro (SEQ ID NO: 25), where this region does not comprise less than about 50% of the peptide.

Another aspect of the invention are complexes comprising at least one cargo compound linked to a variant, derivative or structural equivalent of Laz, Lip or Pan 1 from *Neisseria*, and which facilitate the entry of a linked molecule into a mammalian brain cancer cell or across the blood-brain barrier. In some embodiments, the cargo compound is a cupredoxin, such as azurin, plastocyanin, rusticyanin, pseudoazurin, auracyanin and azurin-like protein, and specifically azurin from *Pseudomonas aeruginosa*. In other embodiments, the complex is modified to extend or optimize the half life of the peptide in the bloodstream. This complex may additionally comprises a cupredoxin-derived transport peptide.

The cargo compound of this complex may be a protein, lipoprotein, polysaccharide, nucleic acid, dye, microparticle, nanoparticle, toxin and drug. In some embodiments, the cargo compound is a protein and the complex is a fusion protein. In other embodiments, the cargo compound is a toxin. The cargo compound may be a therapeutic agent for the treatment of depression, affective disorders, chronic pain, epilepsy, Alzheimer disease, stroke/neuroprotection, brain and spinal cord injury, brain cancer, HIV infection of the brain, various ataxia-producing disorders, amyotrophic lateral sclerosis (ALS), Huntington disease, childhood inborn genetic errors affecting the brain, Parkinson's disease and/or multiple sclerosis. The cargo compound may be a detectable substance, such as one detectable by fluorimetry, microscopy, X-ray CT, MRI and/or ultrasound.

In some embodiments, the complex is in a pharmaceutically suitable carrier. The pharmaceutically suitable carrier may be for intravenous administration. In other embodiments, the pharmaceutically acceptable carrier is appropriate for intracerebroventricular or intracerebral injection.

Another aspect of the invention is a method comprising contacting a cell or cells with a complex comprising at least one cargo compound linked to a variant, derivative or structural equivalent of Laz, Lip or Pan 1 from *Neisseria*, and which facilitates the entry of a linked molecule into a mammalian brain cancer cell or across the blood-brain barrier. The cell may be from a tumor of the central nervous system, specifically astrocytoma, glioblastoma, meningioma, oligodentroglioma, oligoastrocytoma, glioma, ependymoma, spinal cord tumor, ganglioglioma, neurocytoma or medulloblastoma.

Another aspect of the invention is a method of treating a patient with cancer, wherein the complex of the invention is administered to a patient in a therapeutically effective amount. In some embodiments, the complex is administered intravenously, topically, subcutaneously, intramuscularly, or into cell or tumor. In other embodiments, the complex is co-administered with another cancer treatment.

Another aspect of the invention is a method for imaging cancer in a patient comprising administering a complex with a detectable cargo compound to a patient, and detecting location of the cargo compound within the patient. In some cases, the cargo compound is an X-ray contrast agent which is detected by X-ray CT. In other cases, the cargo compound is a magnetic resonance imaging contrast agent which is detected by MRI. In other cases, the cargo compound is an ultrasound contrast agent which is detected by ultrasound imaging.

Another aspect of the invention is a method for diagnosing cancer comprising contacting a cell is contacted with a complex of the invention with a detectable cargo compound and detecting the cargo compound.

Another aspect of the invention is a kit comprising a reagent with an isolated transit peptide which is a variant, derivative or structural equivalent of Laz, Lip or Pan 1 from *Neisseria*, and which facilitates the entry of a linked molecule into a mammalian brain cancer cell or across the blood-brain barrier. In some embodiments, the kit further comprises a reagent comprising a pharmaceutically-acceptable carrier. In other embodiments, the kit comprises a vehicle for administration of the reagent.

Another aspect of the invention are nucleic acid molecules. In some embodiments, the nucleic acids encode an isolated transit peptide which is a variant, derivative or structural equivalent of Laz, Lip or Pan 1 from *Neisseria*, and which facilitates the entry of a linked molecule into a mammalian brain cancer cell or across the blood-brain barrier. In other embodiments, the nucleic acids encode transit peptides comprising a region consisting of at least 4 imperfect or perfect repeats of Ala-Ala-Glu-Ala-Pro (SEQ ID NO: 25), where this region does not comprise less than about 50% of the peptide. In other embodiments, the nucleic acids encode complexes comprising a fusion protein comprising at least one protein cargo compound linked to a transit peptide.

Another aspect of the invention is a method for treating or diagnosing a patient with a condition related to the brain, comprising co-administering to said patient the transit peptide of the invention and at least one cargo compound. In other embodiments, a cupredoxin-derived transport peptide is coadministered with the transit peptide and/or the cargo compound.

BRIEF DESCRIPTION OF THE SEQUENCES

SEQ ID NO: 1 is the genomic DNA coding sequence of the *Neisseria gonorrhoeae* laz gene, Genbank Accession No. Y00530.

SEQ ID NO: 2 is the genomic DNA coding sequence of the *Pseudomonas aeruginosa* azurin gene.

SEQ ID NO: 3 is the genomic DNA coding sequence of the H.8 region of the *Neisseria gonorrhoeae* laz gene.

SEQ ID NO: 4 is the forward primer to PCR amplify the Laz-encoding gene (laz) of *Neisseria gonorrhoeae*.

SEQ ID NO: 5 is the reverse primer to PCR amplify the Laz-encoding gene (laz) of *Neisseria gonorrhoeae*.

SEQ ID NO: 6 is the forward primer to PCR amplify a 3.1 kb fragment of pUC18-laz.

SEQ ID NO: 7 is the reverse primer to PCR amplify a 3.1 kb fragment of pUC18-laz.

SEQ ID NO: 8 is the forward primer to PCR amplify a 0.4 kb fragment of pUC19-laz.

SEQ ID NO: 9 is the reverse primer to PCR amplify a 0.4 kb fragment of pUC19-laz.

SEQ ID NO: 10 is the forward primer to PCR amplify a 3.3 kb fragment of pUC19-laz.

SEQ ID NO: 11 is the reverse primer to PCR amplify a 3.3 kb fragment of pUC19-laz.

SEQ ID NO: 12 is the forward primer to PCR amplify a 0.13 kb fragment of pUC18-laz.

SEQ ID NO: 13 is the reverse primer to PCR amplify a 0.13 kb fragment of pUC18-laz.

SEQ ID NO: 14 is the forward primer to PCR amplify the GST-encoding gene from pGEX-5X-3.

SEQ ID NO: 15 is the reverse primer to PCR amplify the GST-encoding gene from pGEX-5X-3.

SEQ ID NO: 16 is the forward primer to PCR amplify the signal peptide and H.8-encoding region of laz from pUC18-laz.

SEQ ID NO: 17 is the reverse primer to PCR amplify the signal peptide and H.8-encoding region of laz from pUC18-laz.

SEQ ID NO: 18 is the forward primer to PCR amplify the H.8-encoding region from pUC18-laz.

SEQ ID NO: 19 is the reverse primer to PCR amplify the H.8-encoding region from pUC18-laz.

SEQ ID NO: 20 is the forward primer to PCR amplify the GST-H.8 fusion region from pGEX-5X-3-H.8.

SEQ ID NO: 21 is the reverse primer to PCR amplify the GST-H.8 fusion region from pGEX-5X-3-H.8.

SEQ ID NO: 22 is the amino acid sequence of the *Neisseria gonorrhoeae* strain F62 Laz protein, Genbank Accession No. Y00530.

SEQ ID NO: 23 is the amino acid sequence of the *Pseudomonas aeruginosa* azurin.

SEQ ID NO: 24 is the amino acid sequence of the H.8 region from *Neisseria gonorrhoeae* F62 Laz protein.

SEQ ID NO: 25 is the amino acid sequence of a pentapeptide motif.

(A) Cytotoxicity of synthetic H.8 peptide, Paz, Laz and H.8 fusions at the carboxy terminal end of Paz (Paz-H.8) and amino terminal end of the Paz (H.8-Paz) towards glioblastoma LN-229 cells. Cells were treated with the proteins at 3 different concentrations (10, 20 and 40 μM) for 6, 12 and 24 h. MTT assay was done to measure the extent of live cells to account for cytotoxicity (percent cell death). To calculate percentage cytotoxicity, the value of non-treated viable cells was taken to be 100% and the number of viable cells was determined in Paz, Laz and H.8-fusion protein-treated samples. The extent of cytotoxicity (%) was then determined from the number of dead cells. (B) Cytotoxicity of H.8 peptide, Paz, Paz-H.8, H.8-Paz and Laz towards human breast cancer MCF-7 cells. All treatment conditions are similar to (A) above.

Figure 3:
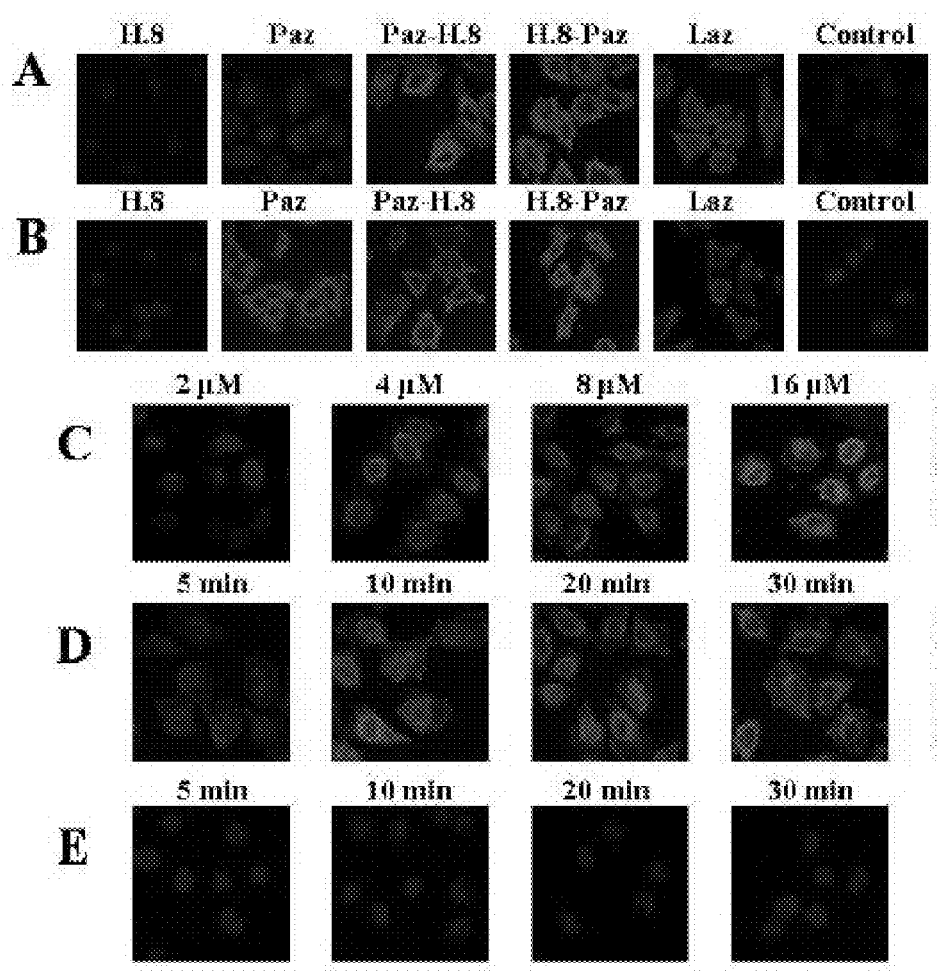

FIG. 3 depicts the entry of various fluorescently labeled azurin-related proteins into glioblastoma LN-229 and breast cancer MCF-7 cells. (A) H.8 peptide, Paz, Paz-H.8, H.8-Paz and Laz (20 μM each) conjugated with Alexa Fluor® 568 was incubated with LN-229 cells on a coverslip at 37° C. for 30 min after which images were taken. (B) Internalization into MCF-7 cells of various proteins conjugated with Alexa Fluor® 568 as visualized by confocal microscopy and as described for (A). (C) Internalization of Laz was visualized by confocal microscopy. Various concentrations (2, 4, 8 and 16 μM) of fluorescently-labeled Laz were incubated with LN-229 cells for 30 min at 37° C. The nucleus is labeled blue with DAPI (4,6-diamidino-2-phenylindole). (D) Laz (10 μM) conjugated with Alexa fluor® 568 was incubated with LN-229 cells for various time periods (5, 10, 20 and 30 min) at 37° C. The internalization was visualized by confocal microscopy. (E) Paz (10 μM) conjugated with Alexa Fluor® 568 was incubated with LN-229 cells on a coverslip at 37° C. for various times after which images were taken. Very little measurable fluorescence was detected in (E).

Figure 4:
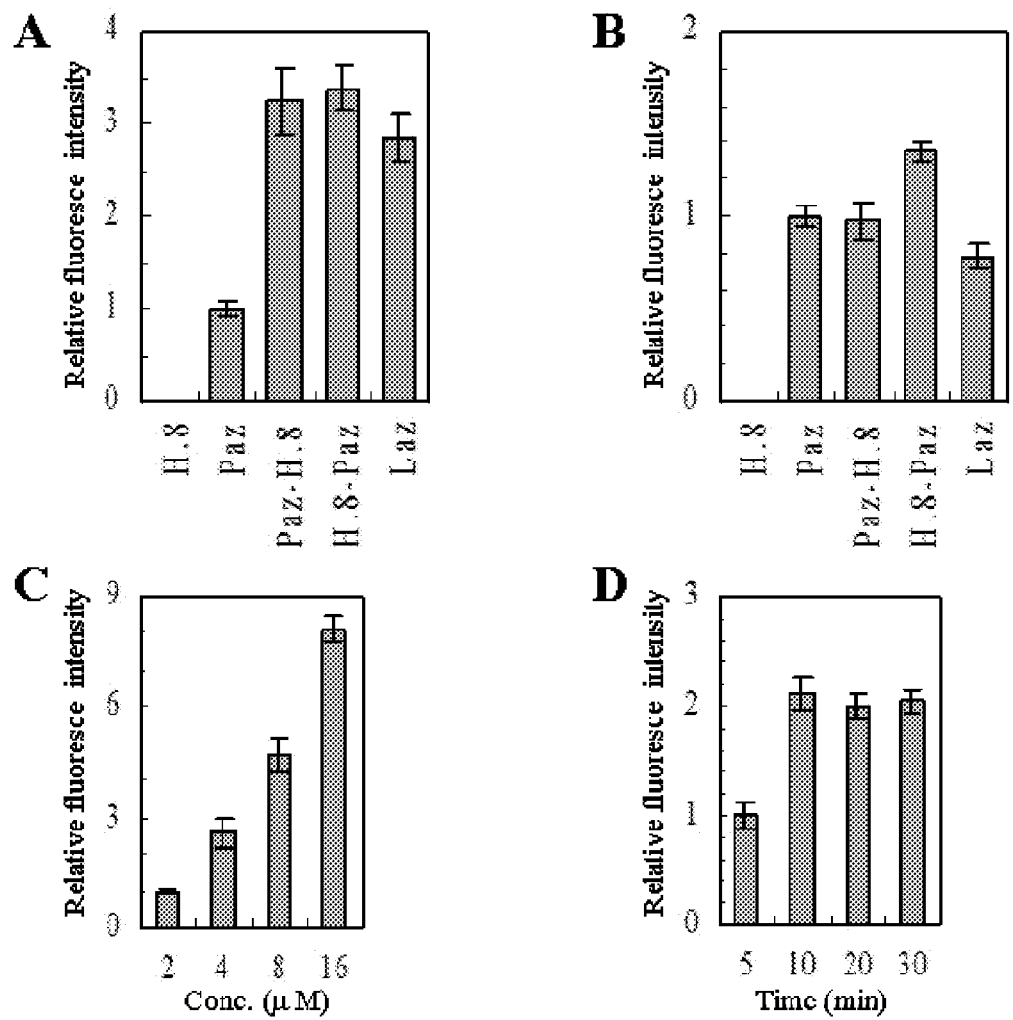

FIG. 4 depicts bar graphs indicating the quantification of the fluorescence found in the confocal microscope images in FIG. 3A-D. (A) Quantification of fluorescence in images in FIG. 3A. Quantification of fluorescence in azurin proteins was done by using Adobe® Photoshop®. Error bars represent the standard deviation of the fluorescence in three different cells in a single sample. (B) Quantification of fluorescence in images in FIG. 3B. Quantification performed as in FIG. 4A. (C) Quantification of fluorescence in images in FIG. 3C. Quantification performed as in FIG. 4A. (D) Quantification of fluorescence in images in FIG. 3D. Quantification performed as in FIG. 4A.

Figure 5:
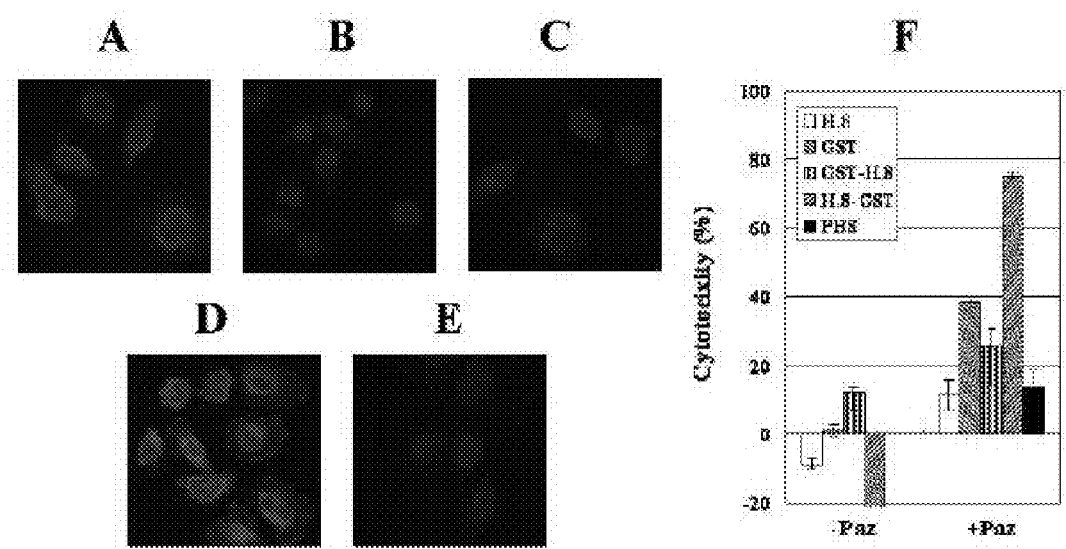

FIG. 5. Combined treatment with H.8-GST fusion proteins facilitates the uptake of Alexa Fluor® 568-labeled Paz in glioblastoma LN-229 cells. Unlabeled 20 μM (A) H.8, (B) GST, (C) GST-H.8, (D) H.8-GST, (E) PBS buffer and 20 μM Paz conjugated with Alexa Fluor® 568 were incubated with LN-229 cells for 30 min at 37° C. The internalization was visualized by confocal microscopy. (F) Cytotoxicity of synthetic H.8 peptide, GST and GST-H.8/H.8-GST fusion derivatives with or without Paz. Approximately 5×10³ LN-229 cells were seeded into 96-well culture plate and treated with 20 μM each of H.8 peptide, GST, GST-H.8, H.8-GST or the same volume of PBS buffer for 24 h with (+Paz) or without (−Paz) 20 μM Paz.

Figure 6:
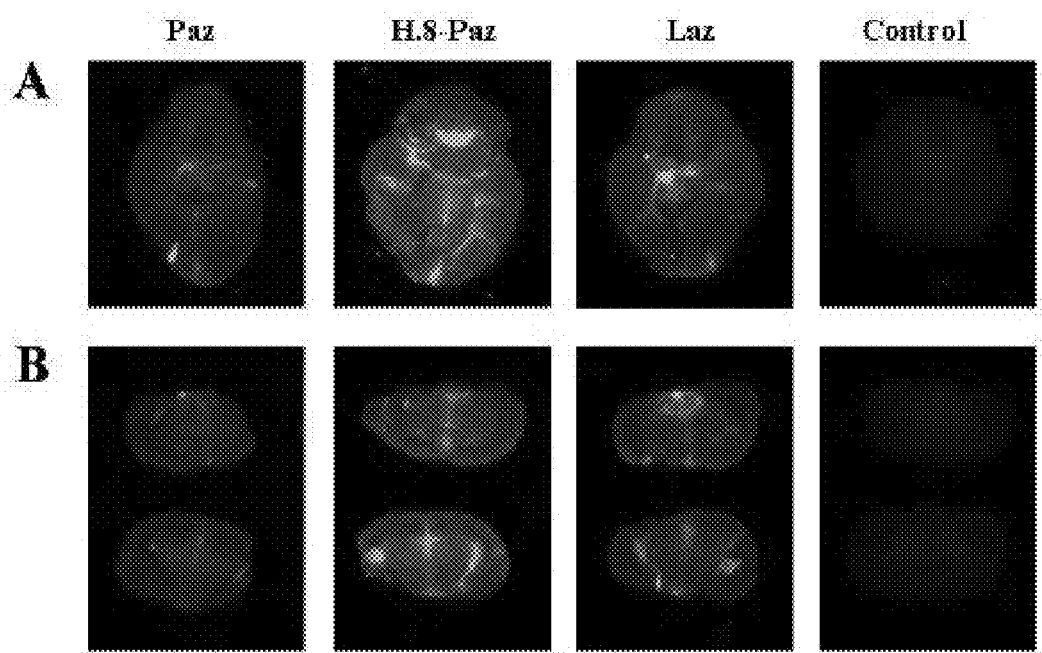

FIG. 6 depicts images of the brains of mice injected with Paz, H.8-Paz and Laz conjugated with IRdye® 800CW (LI-COR Biotechnology, Lincoln, Nebr.). (A) Brain images from live mice. Five hundred μg of Paz, H.8-Paz and Laz conjugated with IRdye® 800CW were injected intraperitoneally in live nude mice. After 24 h, the mice were sacrificed, brains were taken out and the fluorescence was detected and measured with the LI-COR Odyssey® Infrared Imaging System. (B) Rostral mesencephalon region images of nude mice brains treated as in (A). Mice brains were cut horizontally and images were taken.

Figure 7:
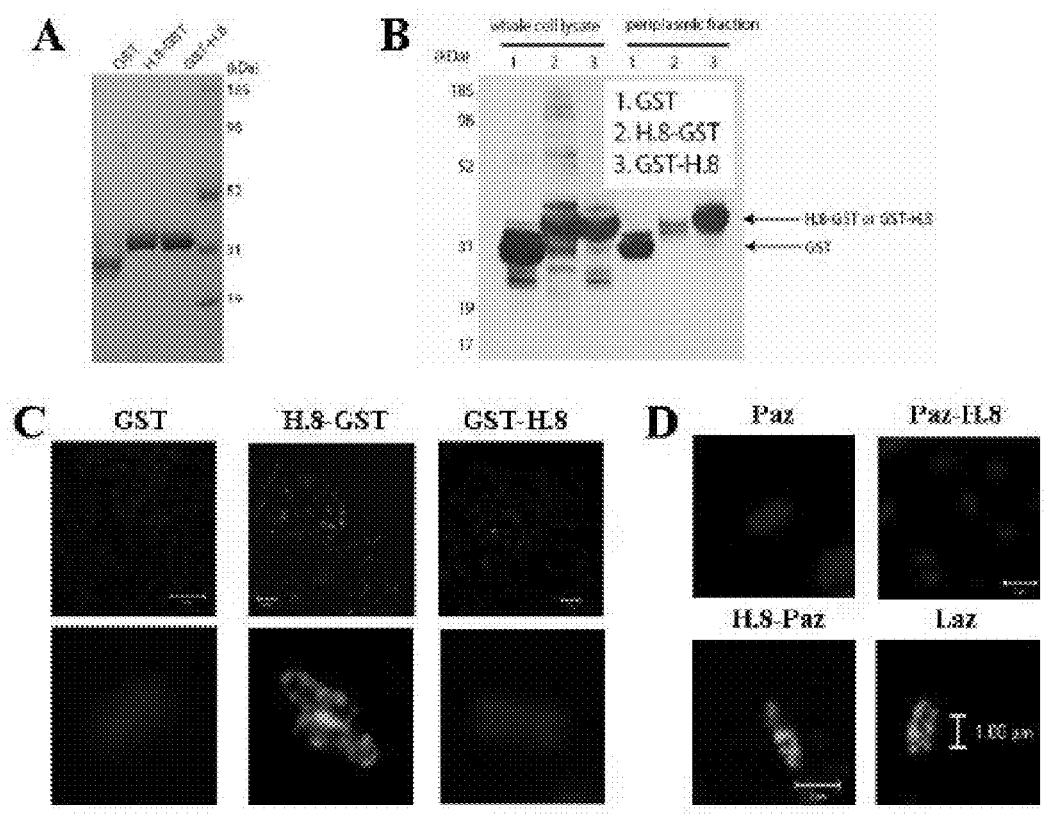

FIG. 7. FIG. 8 depicts SDS-PAGE, Western blotting and confocal microscope images of localization of H.8-Gst fusion proteins in *E. coli*. (A). *E. coli* BL21 (DE3) cells having cloned gst, H.8-gst or gst-H.8 genes were cultured at 37° C. with 0.1 mM IPTG. Cell pellets were washed with PBS twice, and whole cell lysates were run on SDS-PAGE. Coomassie blue staining was used for detection of the proteins. (B). The above procedure was repeated but this time both whole cell lysates and the contents of the periplasmic space were separately isolated, run on SDS-PAGE (20 μg protein) and the GST or GST-H.8 fusion proteins were detected by Western blotting with monoclonal anti-GST antibody to determine the total and the periplasmic concentrations of the proteins. (C). *E. coli* strain BL21(DE) cells harboring cloned gst, H.8-gst or gst-H.8 genes (Table 5) were cultured at 37° C. with 0.4 mM IPTG. One ml each of these bacterial cultures were centrifuged and the resultant bacterial pellets were collected. After washing with PBS twice, one ml of 1% FBS-PBS containing anti-GST antibody (1:2000) was applied. Cell suspensions were incubated for 1 h and then washed with PBS twice. Bacterial cells were incubated with FITC-conjugated anti-rabbit IgG in 1% FBS-PBS for 30 min. To remove unbound antibody, cells were washed again, and fixed with ethanol on ice. *E. coli* samples treated with DAPI (imparting blue coloration) were observed under confocal microscopy (×100 objective), and a single cell was also photographed. (D). *E. coli* cells harboring pUC19-paz (*P. aeruginosa* azurin), pUC19-laz (*Neisseria*), pUC18-H.8-paz or pUC18-paz-H.8 were cultured at 37° C. overnight in presence of 0.1 mM IPTG. 0.5 ml of such cultures were centrifuged and the resultant bacterial pellets were washed with chilled PBS twice. Anti-azurin antibody (1:500) in 1 ml of 1% FBS-PBS was applied and incubated on ice for 1 h. After washing with PBS twice, FITC-conjugated anti-rabbit antibody was applied, incubated on ice for 30 min, washed with PBS twice and fixed with cold ethanol. Bacterial samples were observed by confocal microscopy (×100 objective).

DETAILED DESCRIPTION OF THE EMBODIMENTS

Definitions

As used herein, the term "cell" includes both the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by nontranslation natural process and by entirely synthetic methods as well. A synthetic peptide is one made without the aid of cellular components. Synthetic methods to make peptides are well known in the art and are commercial available. Further, this invention contemplates the use of both the methionine-containing and the methionine-less amino terminal variants of the protein of the invention.

As used herein, the term "condition" includes anatomic and physiological deviations from the normal that constitute an impairment of the normal state of the living animal or one of its parts, that interrupts or modifies the performance of the bodily functions.

As used herein, the term "inhibit cell growth" means the slowing or ceasing of cell division and/or cell expansion. This term also includes the inhibition of cell development or increases in cell death.

As used herein, the term "suffering from" includes presently exhibiting the symptoms of a condition, having a condition even without observable symptoms, in recovery from a condition, and recovered from a condition.

A used herein, the term "treatment" includes preventing, lowering, stopping, or reversing the progression or severity of the condition or symptoms associated with a condition being treated. As such, the term "treatment" includes medical, therapeutic, and/or prophylactic administration, as appropriate.

A "therapeutically effective amount" is an amount effective to prevent, lower, stop or reverse the development of, or to partially or totally alleviate the existing symptoms of a particular condition for which the subject being treated. Determination of a therapeutically effective amount is well within the capability of those skilled in the art.

The term "substantially pure", as used herein, when used to modify a protein or other cellular product of the invention, refers to, for example, a protein isolated from the growth medium or cellular contents, in a form substantially free of, or unadulterated by, other proteins and/or active inhibitory compounds. The term "substantially pure" refers to a factor in an amount of at least about 75%, by dry weight, of isolated fraction, or at least "75% substantially pure." More specifically, the term "substantially pure" refers to a compound of at least about 85%, by dry weight, active compound, or at least "85% substantially pure." Most specifically, the term "substantially pure" refers to a compound of at least about 95%, by dry weight, active compound, or at least "95% substantially pure." The term "substantially pure" may also be used to modify a synthetically make protein or compound of the invention, where, for example, the synthetic protein is isolated from the reagents and by-products of the synthesis reaction(s).

The term "pharmaceutical grade", as used herein, when referring to a peptide or compound of the invention, is a peptide or compound that is isolated substantially or essentially from components which normally accompany the material as it is found in its natural state, including synthesis reagents and by-products, and substantially or essentially isolated from components that would impair its use as a pharmaceutical. For example, a "pharmaceutical grade" peptide may be a isolated from any carcinogen. In some instances, "pharmaceutical grade" my be modified by the intended method of administration, such as "intravenous pharmaceutical grade," in order to specify a peptide or compound that is substantially or essentially isolated from any substance that would render the composition unsuitable for intravenous administration to a patient. For example, an "intravenous pharmaceutical grade" peptide may be isolated from detergents, such as SDS, and anti-bacterial agents, such as azide.

The phrases "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. An "addition" is the removal of one or more amino acids from within the wildtype protein, while a "truncation" is the removal of one or more amino acids from one or more ends of the wildtype protein. Thus, a variant peptide may be made by manipulation of genes encoding the polypeptide. A variant may be made by altering the basic composition or characteristics of the polypeptide, but not at least some of its fundamental activities. For example, a "variant" of the *Neisseria* transit peptide may be a mutated *Neisseria* transit peptide that retains its ability to cross the BBB and/or enter brain cancer cells. In some cases, a variant peptide is synthesized with non-natural amino acids, such as ϵ-(3,5-dinitrobenzoyl)-Lys residues. (Ghadiri & Fernholz, J. Am. Chem. Soc., 112:9633-9635 (1990)). In some embodiments, the variant has not more than 20, 19, 18, 17 or 16 amino acids replaced, deleted or inserted compared to wild-type peptide. In some embodiments, the variant has not more than 15, 14, 13, 12 or 11 amino acids replaced, deleted or inserted compared to wild-type peptide. In some embodiments, the variant has not more than 10, 9, 8 or 7 amino acids replaced, deleted or inserted compared to wild-type peptide. In some embodiments, the variant has not more than 6 amino acids replaced, deleted or inserted compared to wild-type peptide. In some embodiments, the variant has not more than 5 or 4 amino acids replaced, deleted or inserted compared to wild-type peptide. In some embodiments, the variant has not more than 3, 2 or 1 amino acids replaced, deleted or inserted compared to wild-type peptide.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two, three or more carbon atoms, typically one (a) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of a *Neisseria* transit peptide can be a chemically modified *Neisseria* transit peptide that retains its ability to cross the BBB and/or enter brain cancer cells. Chemical modifications of interest include, but are not limited to, amidation, acetylation, sulfation, polyethylene glycol (PEG) modification, phosphorylation or glycosylation of the peptide. In addition, a derivative peptide maybe a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=X/Y*100 where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

General

The present invention relates to methods and materials for delivering a cargo compound across the blood-brain barrier (BBB) and/or into brain cancer cells, and materials and methods for the treatment of cancer of the mammalian brain, as well as other conditions of the brain and central nervous system. As disclosed herein, it is now know that peptide regions composed of repeats of the motif AAEAP (SEQ ID NO: 25) will allow associated or fused peptides and other cargo compound to be transported across the blood-brain barrier and/or into mammalian brain cancer cells. More specifically, the H.8 region of the *Neisseria gonorrhoeae* protein Laz, can be used to transport associated or fused proteins and other cargo compounds across the BBB and/or into brain cancer cells. In addition, it is contemplated that peptides similar to the H.8 region in the use of the AAEAP (SEQ ID NO: 25) pentapeptide repeats can be used to transport proteins and other cargo compound across the BBB and/or into brain cancer cells, such as part or all of the Lip protein and part or all of the Pan 1 protein, both from *Neisseria gonorrhoeae*. Cargo compounds delivered by the present invention include, but are not limited to, proteins, lipoproteins, polysaccharides, nucleic acids, including anti-sense nucleic acids, dyes, fluorescent and radioactive tags, microparticles or nanoparticles, toxins, inorganic and organic molecules, small molecules, and drugs. In some embodiments, the drugs and/or toxins kill tumor cells. In other embodiments, the cargo compounds treat various conditions of the brain.

It is known that many cupredoxin proteins, such as *Pseudomonas aeruginosa* azurin, have the ability to specifically enter and kill many types of mammalian cancer cells. (Yamada et al., Cell. Biol. 7:1418-1431 (2005); Hiraoka et al., PNAS 101:6427-6432 (2004); Hiraoka et al., Biochem. Biophys. Res. Comm. 338:1284-1290 (2005)) It is also known that *P. aeruginosa* azurin is not cytotoxic towards brain cancer cells, such as glioblastoma cells. See Example 2. Surprisingly, it is now known that the Laz protein, an azurin-like protein from *Neisseria gonorrhoeae* and other *Neisseria* species, is able to specifically enter and kill brain cancer cells such as glioblastoma cells, as well as other tumors. See Examples 2 and 7. Furthermore, it is now known that the H.8 region of the Laz protein can confer upon *P. aeruginosa* azurin when fused to either its N-terminal or C-terminal, the ability to enter and kill glioblastoma cells. See Examples 2 and 3.

Also surprisingly, it is now known that the H.8 region does not have to be physically attached to a co-administered protein, such as azurin, to confer upon that protein the ability to enter glioblastmona cells. See Example 5. H.8 and H.8 fused to the N-terminus of GST both increased the entry of physically unattached azurin into glioblastoma cells as compared to azurin alone, however H.8 fused to the C-terminus of GST was ineffective. Further, the H.8 and H.8 fused to the N-terminal of GST when coadministered with azurin both enhanced the cytotoxicity of azurin towards glioblastoma cells. See Example 5.

Surprisingly, the H.8 domain of Laz is now known to confer upon proteins to which it is fused the ability to cross the blood brain barrier in living mice and localize to the brain. See Example 6.

Finally, the H.8 region is now known to be responsible for the surface display of fused proteins in *E. coli*. See Example 7. While GST, and GST with H.8 fused to the C-terminus both accumulate in the periplasmic space of the *E. coli* expressing them, GST with H.8 fused on the N-terminus is transported to the surface of the *E. coli* cells. While not intending to limit the invention to any mechanism of action, ability of the H.8 region to cause the transport of a fused protein to the surface of the bacterial cell may be related to ability of the H.8 region to allow fused proteins to cross the BBB. Since meningococci such as *N. meningitidis* cross the BBB to invade brain meninges (Nassif, et al., id.; Huang & Jong, id.), it is likely such bacteria use surface-exposed cell components to disrupt the BBB. Type IV pili of *N. meningitidis* are implicated in the formation of brain microvilli-like membrane protrusions, and the retraction of such pili is known to play a central role in the interactions between *Neiserria* and human cells. (Pujol et al., PNAS 96:4017-4022 (1999); Merz et al., Nature 407: 98-102 (2002)) However, type IV pili are known to retract following the pili-mediated contact formation with other cells and additional unknown surface components of *N. meningitidis* are thought to be responsible for the crossing of the BBB. (Nassif et al., id.) It is therefore possible that the surface-displayed H.8 region is directly involved with enabling *Neisseria* to cross the BBB and interact with human brain cancer cells.

The Laz H.8 region is 39 amino acid region at the N-terminus of Laz, which contains imperfect AAEAP (SEQ ID NO: 25) pentapeptide repeats. It is contemplated that this AAEAP (SEQ ID NO: 25) repeat unit can be used to design peptides that will transport cargos across the BBB and/or into brain cancer cells. Further, it is contemplated that the amino acid sequence of other outer membrane proteins from *Neisseria gonorrhoeae* and *Neisseria* meningitis with AAEAP (SEQ ID NO: 25) repeats can be used to design peptides that will transport cargo across the BBB and/or into brain cancer cells. Other *Neisseria* outer membrane proteins of interest include, but are not limited to Lip and Pan 1. (Trees et al., J. Clin. Microbiol. 38:2914-2916 (2000); Hoehn and Clark, Infection and Immunity 60:4704-4708 (1992))

The present invention relates to methods and materials for delivering a cargo compound across the blood-brain barrier into the brain and/or into brain cancer cells. Delivery of the cargo compound according to this invention is accomplished by the use of a suitable transit peptide. In one embodiment of the invention, the cargo compound is linked to a *Neisseria* or AAEAP transit peptide of the invention. In another embodiment, the cargo compound is co-administered with a *Neisseria* or AAEAP transit peptide of the invention. In another embodiment, the cargo compound is linked to a cupredoxin-derived transport peptide and a *Neisseria* or AAEAP transit peptide of the invention.

In one embodiment, a cargo compound is delivered to inhibit the cell growth in a cancer cell, such as a brain cancer cell. Such a cancer cell can be from, for example, an astrocytoma, glioblastoma, meningioma, oligodentroglioma, oligoastrocytoma, glioma, ependymoma, spinal cord tumor, ganglioglioma, neurocytoma and medulloblastoma. For example, the cargo compound may be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A, among others. In some embodiments, a biologically active fragment of one of the above classes of compounds is delivered. In another embodiment, the cargo compound is delivered in order to generate an image of the target tissue. For example, the target tissue may be a cancer and the cargo compound can be one commonly used to generate an image for detection by X-ray computed tomography (CT), Magnetic Resonance Imaging (MRI) and ultrasound. In these embodiments, the cargo compound may a gamma ray or positron emitting radioisotope, a magnetic resonance imaging contrast agent, an X-ray contrast agent, and/or an ultrasound contrast agent. In other embodiments, the cargo compound may be delivered to treat a condition related to the brain.

*Neisseria* and AAEAP Transit Peptides

The invention provides for a transit peptide that allows for the transport of linked or associated cargo into mammalian brain cancer cells but not non-cancerous cells, and/or across the BBB. It has been discovered that *Neisseria* outer membrane proteins, such as Laz, comprise a protein transit domain, the H.8 domain, which facilitates the entry of linked cargo into mammalian brain cancer cells and/or across the BBB. The invention provides *Neisseria* transit peptides derived from *Neisseria* outer membrane proteins. The invention further provides natural or synthetic transit domains comprising repeats of the AAEAP (SEQ ID NO: 25) pentapeptide that may be used to transport linked or associated cargo into mammalian brain cancer cells and/or across the BBB.

The term "*Neisseria* transit peptide" refers to all or a fragment of a *Neisseria* outer membrane protein that includes the amino sequence that is required for the entry of a cargo into a brain cancer cell and/or across the BBB. Suitable *Neisseria* outer membrane proteins include, but are not limited to Laz, Lip or Pan 1 from *N. gonorrhoeae*. Of particular interest is Laz from *N. meningitidis* and *N. gonorrhoeae*. Determination of which outer membrane proteins that include an amino sequence that is required for the entry of a cargo into a brain cancer cell and/or across the BBB may be preformed by any method that identifies those peptides required for entry into a brain cancer cell or passage across the BBB. In one such method, all or a fragment of a *Neisseria* outer membrane protein is linked to a marker substance and a test performed to determine whether the all or a fragment of a *Neisseria* outer membrane protein enters a brain cancer cell and/or crosses the BBB. Methods that may be used to identify suitable *Neisseria* outer membrane proteins or fragments thereof are found in Examples 4 and 7.

Suitable *Neisseria* outer membrane proteins which may be used in the invention include outer membrane proteins of a *Neisseria* species that are recognized by the H.8 antibody and/or are comprised of several perfect or imperfect repeats of the AAEAP (SEQ ID NO: 25) motif. In some embodiments, *Neisseria* transit peptides are recognized by the H.8 antibody. The methodology and parameters for determining whether a protein or peptide is recognized by the H.8 antibody are described in Cannon et al., Infection and Immunity 43:994-999 (1984).

The invention also provides AAEAP transit peptides, which are peptides are composed of multiple perfect or imperfect repeats of the AAEAP (SEQ ID NO: 25) motif that may transport linked or associated cargo compounds into mammalian brain cancer cells and/or across the BBB. An "imperfect" repeat as used herein is defined as a repeat of the AAEAP (SEQ ID NO: 25) pentapeptide where at least one of the five amino acids is not part of the AAEAP (SEQ ID NO: 25) motif. In other embodiments, the imperfect repeat may have not more than 1, 2, 3 or 4 amino acids that are not part of the AAEAP (SEQ ID NO: 25) pentapeptide. In some embodiments, the *Neisseria* transit peptide is amino acids 1 to 39 of the Laz protein (SEQ ID NO: 24). In some embodiments, the *Neisseria* transit peptide is at least about 20 amino acids in length, at least about 40 amino acids in length, at least about 60 amino acids in length, or at least about 80 amino acids in length. In other embodiments, the *Neisseria* transit peptide is not more than about 40 amino acids in length, not more than about 100 amino acids in length, not more than about 200 amino acids in length, or not more than about 400 amino acids in length. In some embodiments, the *Neisseria* transit peptide has at least about 90% amino acid sequence identity, at least about 95% amino acid sequence identity or at least about 99% amino acid sequence identity to a *Neisseria* outer membrane protein, such as SEQ ID NO: 22.

The term "AAEAP (SEQ ID NO: 25) transit peptide" refers to a peptide that is comprised a region of perfect and/or imperfect AAEAP (SEQ ID NO: 25) pentapeptide repeats. The AAEAP (SEQ ID NO: 25) transit peptide may be a synthesized by standard methods, or may reproduced by cell-based expression systems. In some embodiments, the AAEAP (SEQ ID NO: 25) transit peptide is comprised of at least 2 AAEAP (SEQ ID NO: 25) pentapeptide repeats, at least 4 AAEAP (SEQ ID NO: 25) pentapeptide repeats, at least 6 AAEAP (SEQ ID NO: 25) pentapeptide repeats, at least 8 AAEAP (SEQ ID NO: 25) pentapeptide repeats, at least 10 AAEAP (SEQ ID NO: 25) pentapeptide repeats, at least 15 AAEAP (SEQ ID NO: 25) pentapeptide repeats or at least 20 AAEAP (SEQ ID NO: 25) pentapeptide repeats. In some embodiments, the AAEAP (SEQ ID NO: 25) transit peptide is comprised of not more than 10 AAEAP (SEQ ID NO: 25) pentapeptide repeats, not more than 20 AAEAP (SEQ ID NO: 25) pentapeptide repeats, not more than 30 AAEAP (SEQ ID NO: 25) pentapeptide repeats, or not more than 40 AAEAP (SEQ ID NO: 25) pentapeptide repeats. In some embodiments, the AAEAP (SEQ ID NO: 25) transit peptide is comprised of only perfect AAEAP (SEQ ID NO: 25) pentapeptide repeats, only imperfect AAEAP (SEQ ID NO: 25) pentapeptide repeats, or a mixture of perfect and imperfect AAEAP (SEQ ID NO: 25) pentapeptide repeats.

In some embodiments, the AAEAP (SEQ ID NO: 25) transit peptide consists of only AAEAP (SEQ ID NO: 25) pentapeptide repeats. In other embodiments, the AAEAP (SEQ ID NO: 25) transit peptide consists of at least about 95% AAEAP (SEQ ID NO: 25) pentapeptide repeats per total length, at least about 90% AAEAP (SEQ ID NO: 25) pentapeptide repeats per total length, at least about 80% AAEAP (SEQ ID NO: 25) pentapeptide repeats per total length, at least about 50% AAEAP (SEQ ID NO: 25) pentapeptide repeats per total length. In some embodiments, the region of repeats is at least about 70% identical, at least about 80% identical, at least about 90% identical, or at least about 95% identical to a peptide comprising an equal number of repeats of Ala-Ala-Glu-Ala-Pro (SEQ ID NO: 25).

In some embodiments, the *Neisseria* transit peptide and/or AAEAP (SEQ ID NO: 25) transit peptide can be used to facilitate the transport linked cargo selectively into brain cancer cells and/or across the BBB. In other embodiments, the *Neisseria* transit peptide and/or AAEAP (SEQ ID NO: 25) transit peptide can be used to transport co-administered cargo into brain cancer cells and/or across the BBB.

Modification of a *Neisseria* or AAEAP Transit Domain

In other embodiments of the present invention, a *Neisseria* transit peptide or AAEAP (SEQ ID NO: 25) transit peptide is chemically modified or genetically altered to produce variants and derivatives that retain the ability to transport a cargo compound into a brain cancer cell or across the BBB.

Variants of a *Neisseria* transit peptide or AAEAP (SEQ ID NO: 25) transit peptide may be synthesized by standard techniques. Derivatives are amino acid sequences formed from native amino acids either directly or by modification or partial substitution. Variants may be analogs, which are amino acid sequences that have a structure similar, but not identical, to the native compound but differ from it in respect to certain components or side chains. Analogs may be synthesized or from a different evolutionary origin. Variants may be full length or other than full length, if the derivative or analog contains a modified amino acid.

The invention provides for amino acid sequence variants of the *Neisseria* transit peptide, which have amino acids replaced, deleted, or inserted as compared to the wild-type polypeptide. Variants of the invention may be truncations of the *Neisseria* transit peptide. As used herein, a "truncation" of a polypeptide is the peptide that results from the removal of at least one amino acid residue from at least one end of the polypeptide sequence. In some embodiments, the truncation peptide results from at least the removal of at least one amino acid residue, at least five amino acid residues, at least 10 amino acid residues, at least 50 amino acid residues, at least 100 amino acid residues, at least 120 amino acid residues or at least 150 amino acid residues from either or both ends of the polypeptide sequence. In some embodiments, the composition comprises a peptide that consists of a region of the *Neisseria* transit peptide that is less that the full length the *Neisseria* transit peptide. In some embodiments, the composition comprises a peptide that consists of more than about 10 residues, more than about 15 residues or more than about 20 residues of a truncated *Neisseria* transit peptide. In some embodiments, the composition comprises a peptide that consists of not more than about 100 residues, not more than about 70 residues, not more than about 50 residues, not more than about 40 residues, or not more than about 30 residues of a truncated *Neisseria* transit peptide.

Variants of a *Neisseria* transit peptide or AAEAP (SEQ ID NO: 25) transit peptide include, but are not limited to, molecules comprising regions that are substantially homologous to the *Neisseria* transit peptide (SEQ ID NO: 24) or AAEAP (SEQ ID NO: 25) transit peptide by at least about 65%, 70%, 75%, 85%, 90%, 95%, 98%, or 99% identity over an amino acid sequence of identical size or when compared to an aligned sequence in which the alignment is performed by a homology algorithm. The term "percent (%) amino acid sequence identity" between a *Neisseria* transit peptide or AAEAP (SEQ ID NO: 25) transit peptide and a candidate sequence is defined as the percentage of amino acid residues in a *Neisseria* transit peptide or AAEAP (SEQ ID NO: 25) transit peptide that are identical to amino acid residues in a candidate sequence when the two sequences are aligned.

The variants also include peptides made with synthetic amino acids not naturally occurring. For example, non-naturally occurring amino acids may be integrated into the variant peptide to extend or optimize the half-life of the composition in the bloodstream. Such variants include, but are not limited to, D,L-peptides (diastereomer), (Futaki et al., J. Biol. Chem. 276(8):5836-40 (2001); Papo et al., Cancer Res. 64(16):5779-86 (2004); Miller et al, Biochem. Pharmacol. 36(1):169-76, (1987)); peptides containing unusual amino acids (Lee et al., J. Pept. Res. 63(2):69-84 (2004)), and olefin-containing non-natural amino acid followed by hydrocarbon stapling (Schafineister et al., J. Am. Chem. Soc. 122:5891-5892 (2000); Walenski et al., Science 305:1466-1470 (2004)). and peptides comprising ϵ(3,5-dinitrobenzoyl)-Lys residues.

In other embodiments, the peptide of the invention is a derivative of a *Neisseria* transit peptide or AAEAP (SEQ ID NO: 25) transit peptide. The derivatives of the transit peptides are chemical modifications of the peptide such that the peptide still retains some of its fundamental activities. For example, a "derivative" of a transit peptide can be a chemically modified transit peptide that retains its ability to cross the BBB and/or enter brain cancer cells. Derivations that result in altered *Neisseria* transit peptide or AAEAP transit peptide activity are contemplated as part of the invention as long as such losses in activity are not appreciable. As used herein, "appreciable loss" is more than about 50% activity as compared to the unaltered peptide. Chemical modifications of interest include, but are not limited to, amidation, acetylation, sulfation, polyethylene glycol (PEG) modification, phosphorylation and glycosylation of the peptide. In addition, a derivative peptide maybe a fusion of a transit peptide, or variant, derivative or structural equivalent thereof to a chemical compound, such as but not limited to, another peptide, drug molecule or other therapeutic or pharmaceutical agent or a detectable probe.

Derivatives of interest include chemical modifications by which the half-life in the bloodstream of the peptides and compositions of the invention can be extended or optimized, such as by several methods well known to those in the art, including but not limited to, circularized peptides (Monk et al., BioDrugs 19(4):261-78, (2005); DeFreest et al., J. Pept. Res. 63(5):409-19 (2004)), N- and C-terminal modifications (Labrie et al., Clin. Invest. Med. 13(5):275-8, (1990)), and olefin-containing non-natural amino acid followed by hydrocarbon stapling (Schafineister et al., J. Am. Chem. Soc. 122: 5891-5892 (2000); Walenski et al., Science 305:1466-1470 (2004)).

It is contemplated that the transit peptides of the invention may be a variant, derivative and/or structural equivalent of a Neisseria transit peptide or AAEAP (SEQ ID NO: 25) transit peptide. For example, the peptides may be a truncation of Neisseria transit peptide that has been PEGylated, thus making it both a variant and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. (Scharmeister et al., J. Am. Chem. Soc. 122:5891-5892 (2000); Walensky et al., Science 305:1466-1470 (2004)). Additionally, peptides that are structural equivalents of a Neisseria transit peptide may be fused to other peptides, thus making a peptide that is both a structural equivalent and a derivative. These examples are merely to illustrate and not to limit the invention.

Changes can be introduced into a Neisseria transit peptide or AAEAP (SEQ ID NO: 25) transit peptide that incur alterations in the amino acid sequences of the a Neisseria transit peptide or AAEAP (SEQ ID NO: 25) transit peptide that do not nullify the ability of the a Neisseria transit peptide or AAEAP (SEQ ID NO: 25) transit peptide to transport a cargo compound into a brain cancer cell and/or across the BBB. A "non-essential" amino acid residue is a residue that can be altered from the sequence of the a Neisseria transit peptide or AAEAP (SEQ ID NO: 25) transit peptide without nullifying its ability to transport a cargo compound into a cell and/or across the BBB whereas an "essential" amino acid residue is required for such activity.

Amino acids for which "conservative" substitutions can be made are well known in the art. Useful conservative substitutions are shown in Table 1, "Preferred substitutions." Conservative substitutions whereby an amino acid of one class is replaced with another amino acid of the same class fall within the scope of the invention so long as the substitution does not nullify the activity of the Neisseria/AAEAP transit peptide. Such exchanges that result in altered Neisseria/AAEAP transit peptide activity are contemplated as part of the invention so long as such a loss of activity is not appreciable. As used herein, an "appreciable loss" is more than about 50% of the activity as compared to the unaltered peptide.

TABLE 1

Preferred substitutions

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

"Non-conservative" substitutions that affect (1) the structure of the polypeptide backbone, such as a β-sheet or α-helical conformation, (2) the charge, (3) hydrophobicity, or (4) the bulk of the side chain of the target site can modify the Neisseria/AAEAP transit peptide function. Residues are divided into groups based on common side-chain properties as denoted in Table 2. Non-conservative substitutions entail exchanging a member of one of these classes for another class.

Non-conservative substitutions whereby an amino acid of one class is replaced with another amino acid of a different class fall within the scope of the invention so long as the substitution does not nullify the activity of the Neisseria transit peptide or AAEAP (SEQ ID NO: 25) transit peptide. Such exchanges that result in altered Neisseria transit peptide or AAEAP (SEQ ID NO: 25) transit peptide activity are contemplated as part of the invention so long as such losses in activity are not appreciable.

TABLE 2

Amino acid classes

| Class | Amino acids |
| --- | --- |
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

In other embodiments, the invention contemplates structural equivalents of the Neisseria transit peptides or AAEAP (SEQ ID NO: 25) transit peptides which have a significant structural similarity to Neisseria gonnorhoeae Laz amino acid residues 1 to 39 (SEQ ID NO: 24). Specifically, significant structural homology between a structural equivalent of the Neisseria transit peptide and Neisseria gonnorhoeae Laz amino acid residues 1 to 39 (SEQ ID NO: 24) may be determined by using the VAST algorithm (Gibrat et al., Curr Opin Struct Biol 6:377-385 (1996); Madej et al., Proteins 23:356-3690 (1995)). In specific embodiments, the VAST p value from a structural comparison of a structural equivalent of a Neisseria transit peptide or AAEAP (SEQ ID NO: 25) transit peptide and Neisseria gonnorhoeae Laz amino acid residues 1 to 39 (SEQ ID NO: 24) is less than about $10^{-3}$, less than about $10^{-5}$, or less than about $10^{-7}$. In other embodiments, significant structural homology between a structural equivalent of the Neisseria transit peptide and Neisseria gonnorhoeae Laz amino acid residues 1 to 39 (SEQ ID NO: 24) can be determined by using the DALI algorithm (Holm & Sander, J. Mol. Biol. 233:123-138 (1993)). In specific embodiments, the DALI Z score for a pairwise structural comparison is at least about 3.5, at least about 7.0, or at least about 10.0.

Modifications to a Neisseria transit peptide or AAEAP (SEQ ID NO: 25) transit peptide can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-50 (1987)), cassette mutagenesis, restriction selection mutagenesis (Wells et al., Gene 34:315-23 (1985)) or other known techniques can be performed on the cloned DNA to produce a Neisseria/AAEAP transit peptide variant encoding nucleic acid. In addition, nucleotides encoding a Neisseria transit peptide or AAEAP (SEQ ID NO: 25) transit peptide variants may be synthesized by methods that are well known in the art.

Neisseria/AAEAP (SEQ ID NO: 25) Transit Peptide—Cargo Compound Complex

In another aspect of the invention, provided are transit peptide-cargo complexes, where Neisseria transit peptide or a AAEAP transit peptide are complexed with at least on cargo compound. The transit peptides of these complexes may be either a Neisseria transit peptide, a AAEAP (SEQ ID NO: 25) transit peptide, or variants, derivatives or structural equivalent of either. Cargo compounds delivered by the present invention include, but are not limited to, proteins, lipoproteins, polysaccharides, nucleic acids, including anti-sense nucleic acids, dyes, microparticles or nanoparticles, toxins, organic and inorganic molecules, small molecules, and drugs. Such transit peptide-cargo complexes may be used to deliver drugs into the brain, and/or brain cancer cells, and cancer cells in general, for therapeutic purposes, to deliver imaging compounds to brain cancer cells, and cancer cells in general, for diagnostic purposes, and any other purpose that requires the deliver of a specific compound into the brain, and/or into brain cancer cells. Cargo compounds may be attached to the C-terminus or N-terminus of the transit peptide.

In some embodiments, the Neisseria transit peptide or the AAEAP transit peptide is complexed with a cupredoxin-derived transport peptide. Cupredoxin-derived transport peptides are provided in U.S. patent application Ser. No. 11/244,105, filed Oct. 6, 2005, which is hereby expressly incorporated by reference. In some embodiments, the cupredoxin-derived transport peptide is, comprises the 50-77 amino acid region of Pseudomonas aeruginosa azurin, of is a variant, derivative or structural equivalent thereof.

As used herein, the terms "complexed," "complex" or "linked" refer to the physical association between the components being complexed. In some cases, the physical association may not be direct, but may be mediated by a linking group or another component. Components may be proteins, other organic molecules or inorganic molecules, among others. The physical association between the components may be by covalent bonds, hydrophobic bonds and/or van der waals forces, or any other means that holds the components in physical association.

In various embodiments of the present invention, the cargo compound may comprise a cupredoxin which is cytotoxic to cancer cells, such as azurin: from P. aeruginosa (SEQ ID NO: 24)("wt-azurin"); plastocyanin from the cyanobacterium Phormidium laminosum; rusticyanin from Thiobacillus ferrooxidans; pseudoazurin from Achromobacter cycloclastes, azurins from Pseudomonas syringa, Neisseria meningitidis, Vibrio parahaemolyticus, Bordetella bronchiseptica, auracyanin A and B from Chloroflexus aurantiacus or Neisseria gonorrhoeae, among other azurin and azurin-like proteins. In other embodiments, the cargo compound may be a cytochrome c, such as cytochrome $c_{551}$ from P. aeruginosa. In other embodiments, the cargo compound may be a variant of any of the above that retains its cytotoxicity in cancer cells.

In one embodiment, the cargo compound may be a detectable substance, for example, a fluorescent substance, such as green fluorescent protein; a luminescent substance; an enzyme, such as β-galactosidase; or a radiolabelled or biotinylated protein is delivered to confer a detectable phenotype to a cell. Similarly, microparticles or nanoparticles labeled with a detectable substance, for example, a fluorescent substance, can be delivered. One example of suitable nanoparticles is found in U.S. Pat. No. 6,383,500, issued May 7, 2002, which is hereby expressly incorporated by reference. Many such detectable substances are known to those skilled in the art.

In some embodiments, the cargo compound may be a detectable substance that is suitable for X-ray computed tomography, magnetic resonance imaging, ultrasound imaging or radionuclide scintigraphy. In these embodiments, the cargo compound is administered to the patient for purposes of diagnosis. A contrast agent is administered as a cargo compound to enhance the image obtained by X-ray CT, MRI and ultrasound. In various embodiments, the cargo compound is a gamma ray or positron emitting radioisotope, a magnetic resonance imaging contract agent, an X-ray contrast agent, and/or an ultrasound contrast agent.

The administration of a radionuclide cargo compound that is targeted to brain tumor tissue via a Neisseria/AAEAP (SEQ ID NO: 25) transit peptide, with or without a cupredoxin-derived transport peptide, can be used for radionuclide scintigraphy. In some embodiments, a Neisseria/AAEAP (SEQ ID NO: 25) transit peptide may contain the radionucleotide with or without a cargo compound. U.S. Pat. Pub. No. 2006/0039861 provides peptide-targeted, multimeric contrast agents for use as radionuclide contrast agents. Commercially available cargo compounds suitable for X-ray imaging include, but are not limited to Visipaque® (iodixanol), Omnipaque® (iohexyl) and Imagopaque®, available from GE Healthcare (Chalfont St. Giles, United Kingdom).

The administration of a ultrasound contrast agent cargo compound that is targeted to brain tumor tissue via a Neisseria/AAEAP (SEQ ID NO: 25) transit peptide, with or without a cupredoxin-derived transport peptide, can be used for ultrasound imaging. Ultrasound contrast agents suitable for use as cargo compounds include, but are not limited to, a microbubble of a biocompatible gas, a liquid carrier, and a surfactant microsphere, further comprising an optional linking moiety, $L_n$, between the targeting moieties and the microbubble. Microbubbles of interest include, but are not limited to, those provided in Table 3. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein expressly incorporated by reference. The term surfactant microsphere includes nanospheres, liposomes, vesicles and the like. In some embodiments, the ultrasound contrast agent is a liposome or dextran. The biocompatible gas may be air, or a fluorocarbon, such as a $C_3$-$C_5$ perfluoroalkane, which provides the difference in echogenicity and thus the contrast in ultrasound imaging. The gas may be encapsulated or contained in the microsphere to which is attached the Neisseria/AAEAP (SEQ ID NO: 25) transit peptide, optionally via a linking group. The attachment can be covalent, ionic or by van der Waals forces.

TABLE 3

Microbubbles and their composition to be used as ultrasound contrast agents.

| Microbubble | Gas | Stabilizing shell |
|---|---|---|
| First generation, non-transpulmonary vascular | | |
| Free microbubbles | Air | None |
| Echovist ® (SHU 454) | Air | None |

TABLE 3-continued

Microbubbles and their composition to be used as ultrasound contrast agents.

| Microbubble | Gas | Stabilizing shell |
| --- | --- | --- |
| Second generation, transpulmonary vascular, short half-life (<5 min) | | |
| Albunex ® | Air | Albumin |
| Levovist (SHU 508 A) | Air | Palmitic acid |
| Third generation, transpulmonary vascular, longer half-life (>5 min) | | |
| Aerosomes (Definity, MRX115, DMP115) | Perfluoropropane | Phospholipids |
| Echogen (QW3600) | Dodecafluoropentane | Surfactant |
| Optison ® (FSO 69) | Octafluoropropane | Albumin |
| PESDA | Perfluorobutane | Albumin |
| Quantison | Air | Albumin |
| QW7437 | Perfluorocarbon | Surfactant |
| Imavist ® (Imagent, AFO150) | Perfluorohexane | Surfactant |
| Sonovue ® (BR1) | Sulphur hexafluoride | Phospholipids |
| Transpulmonary with organ-specific phase (live, spleen) | | |
| BR14 | Perfluorobutane | Phospholipids |
| Lenovist (SHU 508 A) | Air | Palmitic acid |
| Sonavist ® (SHU 563 A) | Air | Cyanoacrylate |
| Sonazoid ® (NC100100) | Perfluorocarbon | Surfactant |

The administration of an X-ray contrast agent cargo compound that is targeted to brain tumor tissue via a *Neisseria*/AAEAP (SEQ ID NO: 25) transit peptide, with or without a cupredoxin-derived transport peptide, can be used for X-ray computed tomography, and other forms of X-ray imaging. Current commercial X-ray contrast agents suitable to be used as cargo compounds can be sorted into two categories: 1) ionic contrast agents, having an ionic carboxyl group and 2) non-ionic contrast agents, which do not contain any ionic groups. Examples of commercially available ionic contrast agents include Hypaque® (Diatrizoate) and Hexabrix® (Ioxaglate), while non-ionic agents include Omnipaque® (Iohexyl), Isovue® (Iopamidol), Optiray® (Ioversol), and Visipaque® (Iodixanol). Other X-ray contrast agents suitable for use as cargo compounds include, but are not limited to, one or more X-ray absorbing or "heavy" atoms of atomic number 20 or greater, further comprising an optional linking moiety, $L_n$, between the *Neisseria*/AAEAP (SEQ ID NO: 25) transit peptide and the X-ray absorbing atoms. The frequently used heavy atom in X-ray contrast agents is iodine. X-ray contrast agents comprised of metal chelates (e.g., U.S. Pat. No. 5,417,959) and polychelates comprised of a plurality of metal ions (e.g., U.S. Pat. No. 5,679,810) have been disclosed. Multinuclear cluster complexes have been disclosed as X-ray contrast agents (e.g., U.S. Pat. No. 5,804,161, PCT WO91/14460, and PCT WO 92/17215). Other X-ray contrast agents will be well know to those of skill in the art and can be used as well as cargo compounds in the present invention.

The administration of an MRI contrast agent cargo compound that is targeted to brain tumor tissue via a *Neisseria*/AAEAP (SEQ ID NO: 25) transit peptide, with or without a cupredoxin-derived transport peptide, can be used for MRI imaging. MRI contrast agents suitable for use as cargo compounds include, but are not limited to, one or more paramagnetic metal ions, further comprising an optional linking moiety, $L_n$, between the *Neisseria*/AAEAP (SEQ ID NO: 25) transit peptide and the paramagnetic metal ions. Metals ions of the metal chelates may be paramagnetic ions. Suitable metal ions include those having atomic numbers of 22-29 (inclusive), 42, 44 and 58-70 (inclusive) and have oxidation states of +2 or +3. Examples of such metal ions are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III). Commercially available MRI contrast agents suitable for use as cargo compounds include, but are not limited to Omniscan® (gadodiamide) and Teslascan® from GE Healthcare (Chalfont St. Giles, United Kingdom).

In another embodiment, a cargo compound is delivered to kill or inhibit the growth of a cell, such as a brain cancer cell or other cancer cell. For example, the cargo compound may be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A. In other embodiments, a biologically active fragment of one of the above classes of compounds may be delivered.

In yet another embodiment, the cargo compound is a drug used to treat cancer. Such drugs include, for example, 5-fluorouracil; Interferon α; Methotrexate; Tamoxifen; and Vincrinstine. Other cargo compounds suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5alpha-reductase inhibitors; inhibitors of 17beta-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol™), docetaxel (Taxotere™), and their analogs, and epothilones, such as epothilones A-F and their analogs; plant-derived products, such as vinca alkaloids, epipodophyllotoxins, taxanes; and topoisomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Examples of anticancer and other cytotoxic agents useful as cargo compounds include the following: epothilone derivatives as found in German Patent Nos. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029, the compounds of which can be employed together with any NHR modulators such as AR modulators, ER modulators, with LHRH modulators, especially in the treatment of cancer.

Other examples of cargo compounds include those that can advantageously be delivered to the brain. Such cargo compounds include drugs and other therapeutics for treating conditions related to the brain. Such brain-related conditions include, but are not limited to, depression, affective disorders, chronic pain, epilepsy, Alzheimer disease, stroke/neuroprotection, brain and spinal cord injury, brain cancer, HIV infection of the brain, various ataxia-producing disorders, amyotrophic lateral sclerosis (ALS), Huntington disease, childhood inborn genetic errors affecting the brain, Parkinson's disease and multiple sclerosis.

Antidepressants drugs that may be used as cargo compounds to treat depression and affective disorders include but are not limited to tricyclic antidepressants such as nortriptyline, venlafaxine (Effexor®) and nefazadone (Serzone®); selective serotonin reuptake inhibitors (SSRIs), such as fluoxetine (Prozac®), sertraline (Zoloft®), fluvoxamine (Luvox®), paroxetine (Paxil®), and citalopram (Celexa®), sedating mirtazepine (Remeron®) and the more activating bupropion (Wellbutrin®). Also of interest are headache and migraine medications including but not limited to ergotamine, dihydroergotamine, ketoprofen, propranolol, timolol, atenolol, metoprolol and nadolol.

Drugs that can be used as cargo compounds to treat chronic pain include but are not limited to common pain relievers such as acetaminophen (Tylenol®); anti-inflammatory drugs such as aspirin; non-steroidal anti-inflammatory drugs (NSAIDs) such as ibuprofen (Advil®, Motrin®) and naproxen (Aleve®); opioid pain medications such as morphine-like opioids; antidepressants and anti-seizure medications.

Drugs that can be used as cargo to treat epilepsy include but are not limited to phenobarbital, diphenylhydantoin, trimethadione (Tridione®), diazepam (Valium®), carbamazepine (Tegretol®), valproic acid (Depakene®), Emeside® (ethosuximide), Zarontin® (ethosuximide), trileptal, carbamazepine, Keppra® (levetiracetam), lamictal, acetazolamide, triagabine, sodium valproate, pregabalin, clonazepam, carbamazepine, topiramate, valproic acid, lamotrigine, ethosuximide, clobazam, vigabatrin, levetiracetam, gabapentin, zonisamide, primidone, phenyloin, and oxcarbazepine.

Drugs that can be used as cargo compounds to treat Alzheimer disease include but are not limited to cholinesterase inhibitors, such as Razadyne® (formerly known as Reminyl®) (galantamine), Exelon® (rivastigmine), Aricept® (donepezil), Cognex® (tacrine), and an N-methyl D-aspartate (NMDA) antagonist, Namenda® (memantine).

Drugs that can be used as cargo compounds to treat stroke or for neuroprotection include but are not limited to Gavestinel®, erythropoietin (EPO), thrombopoietin, TNF-alpha, estrogens, melatonin, and cannabinoids.

Drugs that can be used as cargo compounds to treat HIV infection of the brain include but are not limited to non-nucleoside reverse transcriptase inhibitors (NNRTIs) such as delavardine, efavirenz, and nevirapine; nucleoside reverse transcriptase inhibitors (NRTIs) such as abacavir, abacavir, lamivudine, abacavir, lamivudine, zidovudine, didanosine, emtricitabine, emtricitabine, tenofovir DF, lamivudine, lamivudine, zidovudine, stavudine, tenofovir DF, zalcitabine, and zidovudine; protease inhibitors (PIs) such as amprenavir, atazanavir, fosamprenavir, indinavir, lopinavir, ritonavir, nelfinavir, ritonavir, saquinavir, and tipranavir; and fusion inhibitors such as enfuvirtide.

Drugs that can be used as cargo compounds to treat amyotrophic lateral sclerosis (ALS) include but are not limited to creatine, Myotrophin®, Celebrex®, Neotrogin®, NAALADase, neurodex, Rilutek®, oxandrolone, coenzyme Q10, topiramate (Topamax®), xaliproden, indinavir, minocycline, and buspirone.

Drugs that can be used as cargo compounds to treat Huntington disease include but are not limited to antipsychotic drugs, such as haloperidol, or other drugs, such as clonazepam, anti-depressants such as fluoxetine, sertraline and nortriptyline; tranquilizers and lithium; minocycline, citalopram, and Ethyl-EPA (Miraxion®).

Drugs that can be used as cargo compounds to treat Parkinson's Disease include but are not limited to anticholinergics or amantadine, levodopa (L-dopa), bromocriptine, pergolide, pramipexole, ropinirole, selegiline, and amantadine.

Drugs that can be used as cargo compounds to treat multiple sclerosis include but are not limited to adrenocorticotropic hormone (better known as ACTH), prednisone, prednisolone, methylprednisolone, betamethasone, dexamethasone, beta interferon (Avonex®, Betaseron® and Rebif®), alpha interferon, Novantrone® (mitoxantrone), cyclosporine (Sandimmune®), cyclophosphamide (Cytoxan®), methotrexate, azathioprine (Imuran®) and cladribine (Leustatin®)).

In yet another embodiment, the cargo compound is a nucleic acid coding for one of the above classes of compounds.

The above examples are provided for illustration only, many other such compounds are known to those skilled in the art.

Nucleic Acids Coding for a *Neisseria* Transit Domain or AAEAP Transit Domain, or Either Linked to a Cargo Compound In another aspect, the present invention provides nucleic acid molecules encoding the *Neisseria*/AAEAP (SEQ ID NO: 25) transit peptides and variants thereof, or fusion proteins comprising a *Neisseria*/AAEAP (SEQ ID NO: 25) transit peptide linked to a cargo compound where the cargo compound is a protein. The nucleic acid molecule according to the invention can be prepared by a combination of known techniques in the art. The coding sequences used in these nucleic acids may be those found in the native genomic DNA encoding the particular peptide, or may be designed from known codons. These coding sequences may also be designed to take into account alternate codon usage and preferred codon usage of the organism in which the peptide is to be expressed. The nucleic acid sequences for the *Neisseria*/AAEAP (SEQ ID NO: 25) transit peptide and the transit peptide-cargo complexes may individually be prepared by chemical synthesis or cloning. The nucleic acid sequences may be then ligated together with ligase in order to give a nucleic acid molecule of interest.

Methods of Delivering a Cargo Compound using a *Neisseria* or AAEAP Transit Domain The compositions of the invention can be used in, for example, the detection or imaging of a cell type, in the treatment of cancer, particularly of the central nervous system or brain, or in the treatment of a condition related to the brain. The compositions may be administered in an therapeutically effective amount. Typically, the host organism is a mammal, such as a human or animal.

In some embodiments, the cargo compound is delivered complexed to a *Neisseria*/AAEAP (SEQ ID NO: 25) transit peptide, while in other embodiments, the cargo compound is co-administered with the a *Neisseria*/AAEAP (SEQ ID NO: 25) transit peptide but is not complexed to it. More than one cargo compound may be co-administered with a *Neisseria*/AAEAP transit peptide. Co-administration of the cargo compound may be contemporaneous with the administration of the transit peptide, either in the same pharmaceutical preparation or in another pharmaceutical preparation administered within about one hour of administering the transit peptide. In addition, the co-administration of the *Neisseria*/AAEAP (SEQ ID NO: 25) transit peptide and cargo compound may include an administration of the *Neisseria*/AAEAP (SEQ ID NO: 25) transit peptide that takes place more than about one hour but less that about two hours, four hours, six hours, twelve hours or twenty-four hours from the administration of the cargo compound. In some embodiments, a *Neisseria*/AAEAP transit peptide, cargo compound(s) and a cupredoxin-derived transport peptide may be coadministered. In other embodiments, a *Neisseria*/AAEAP transit peptide may be coadministered with a cupredoxin-derived transport peptide complexed with cargo compound(s).

In other various embodiments of the present invention, a *Neisseria*/AAEAP (SEQ ID NO: 25) transit peptide delivers a cargo compound into a cell in vitro, ex vivo or in vivo. For example, delivery may be achieved in vitro by adding a complex of a *Neisseria*/AAEAP (SEQ ID NO: 25) transit peptide and a cargo compound to a cell culture, such as a biopsy. Alternatively, delivery may be achieved ex vivo by adding the complex to a sample removed from a patient, for example, blood, tissue, or bone marrow, and returning the treated sample to the patient. Delivery may also be achieved by administration of the complex directly to a patient. The methods of the present invention may be used for therapeutic, prophylactic, diagnostic or research purposes.

Compositions containing a *Neisseria*/AAEAP (SEQ ID NO: 25) transit peptide, including complexes comprising a *Neisseria*/AAEAP (SEQ ID NO: 25) transit peptide may be administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary administration) or by either intracerebroventricular or intracerebral injection. The compositions of the invention and pharmaceutical formulations thereof can be administered in any amount effective to achieve its intended purpose. When administrated to treat cancer, or any other condition requirement treatment, the composition is administered in a therapeutically effective amount. Guidance for the dosage and administration schedule of various cargo compounds may be gathered from the many references which describe the use of such compounds in treatment or diagnosis, such as the Physicians' Desk Reference (PDR), or as otherwise determined by one of ordinary skill in the art.

The compositions of the invention may be sterilized by conventional, well-known sterilization techniques, or may be sterile filtered. The resulting aqueous solutions may be packaged for use as is, or lyophilized, the lyophilized preparation being combined with a sterile solution prior to administration.

When administering the *Neisseria*/AAEAP (SEQ ID NO: 25) transit peptides, cargo compounds and/or transit peptide-cargo compound complexes in accordance with the present invention in an intravenous manner, the administration may be by intravenous drip or intermittent infusion.

The exact formulation, route of administration, and dosage is determined by the attending health care provider or physician in view of the patient's condition. Dosage amount and interval can be adjusted individually to provide plasma levels of the compositions of the invention which are sufficient to maintain therapeutic effect. Generally, the desired composition is administered in an admixture with a pharmaceutical carrier selected with regard to the intended route of administration and standard pharmaceutical practice.

The appropriate dosage may vary depending upon, for example, the compound containing the *Neisseria*/AAEAP (SEQ ID NO: 25) transit peptide employed, the cargo compound(s), the host, the mode of administration and the nature and severity of the conditions being treated or diagnosed. However, in one embodiment of the methods of the present invention, satisfactory treatment results in humans are indicated to be obtained at daily dosages from about 0.001 to about 20 mg/kg of body weight of the compound containing a *Neisseria*/AAEAP (SEQ ID NO: 25) transit peptide, or a *Neisseria*/AAEAP transit peptide complex. In one embodiment, an indicated daily dosage for treatment in humans may be in the range from about 0.7 mg to about 1400 mg of a compound containing the *Neisseria*/AAEAP (SEQ ID NO: 25) transit peptide or a *Neisseria*/AAEAP transit peptide complex conveniently administered, for example, in daily doses, weekly doses, monthly doses, and/or continuous dosing. Daily doses can be in discrete dosages from 1 to 12 times per day or more. Alternatively, doses can be administered every other day, every third day, every fourth day, every fifth day, every sixth day, every week, and similarly in day increments up to 31 days or more. Dosing can be continuous, intermittent or a single dose, using any applicable dosing form, including tablet, patches, i.v. administration and the like. More specifically, the composition is administered in a therapeutically effective amount. In specific embodiments, the therapeutically effective amount is from about 0.01-20 mg/kg of body weight. In specific embodiments, the dose level is about 10 mg/kg/day, about 15 mg/kg/day, about 20 mg/kg/day, about 25 mg/kg/day, about 30 mg/kg/day, about 35 mg/kg/day, about 40 mg/kg/day, about 45 mg/kg/day or about 50 mg/kg/day.

The method of introducing compositions containing the *Neisseria*/AAEAP (SEQ ID NO: 25) transit peptide(s) or a *Neisseria*/AAEAP transit peptide complex to patients is, in some embodiments, co-administration with other drugs known to treat cancer. Such methods are well-known in the art. In a specific embodiment, the compositions containing the *Neisseria*/AAEAP (SEQ ID NO: 25) transit peptide or a *Neisseria*/AAEAP transit peptide complex are part of an cocktail or co-dosing containing or with other drugs for treating cancer. Such drugs include any of the cargo compounds listed herein for the treatment of cancer.

Pharmaceutical compositions comprising the compositions of the invention may be used in accordance with the present invention can be formulated in a conventional manner using one or more physiologically acceptable carriers comprising excipients and auxiliaries that facilitate processing of the composition, active agents, for inhibiting or stimulating the secretion of the composition, or a mixture thereof into preparations which can be used therapeutically.

Nucleic acid molecules encoding a Neisseria/AAEAP transit peptide or a fusion protein combining a either transit peptide and a cargo compound(s) and/or a cupredoxin-derived transport peptide can be inserted into vectors and used as gene therapy vectors. Gene therapy vectors can be delivered to a subject by, for example, intravenous injection, local administration (U.S. Pat. No. 5,328,470), or by stereotactic injection. (Chen et al., Proc Natl Acad Sci USA, 91:3054-57 (1994)) The pharmaceutical preparation of a gene therapy vector can include an acceptable diluent or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

In one aspect, the composition is delivered as DNA such that the complex is generated in situ. In one embodiment, the DNA is "naked," as described, for example, in Ulmer et al., Science 259:1745-49 (1993) and reviewed by Cohen, Science 259 1691-92 (1993). The uptake of naked DNA may be increased by coating the DNA onto a carrier, e.g. a biodegradable bead, which is efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of the composition. In expression vectors, the introduced DNA is operably-linked to elements such as promoters that signal to the host cell to transcribe the inserted DNA. Some promoters are exceptionally useful, such as inducible promoters that control gene transcription in response to specific factors. Operably-linking a composition polynucleotide to an inducible promoter can control the expression of the Neisseria/AAEAP transit peptide composition polypeptide or fragments. Examples of classic inducible promoters include those that are responsive to α-interferon, heat shock, heavy metal ions, and steroids such as glucocorticoids (Kaufman, Methods Enzymol. 185:487-511 (1990)) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, enhancer elements, promoters, and transcription termination sequences.

Pharmaceutical Compositions Containing a Neisseria Transit Domain

Pharmaceutical compositions of the invention containing a Neisseria/AAEAP (SEQ ID NO: 25) transit peptide or a complex of a Neisseria/AAEAP (SEQ ID NO: 25) transit peptide linked to a cargo compound can be manufactured in any conventional manner, e.g., by conventional mixing, dissolving, granulating, dragee-making, emulsifying, encapsulating, entrapping, or lyophilizing processes. The Neisseria/AAEAP transit peptide complex can be readily combined with a pharmaceutically acceptable carrier well-known in the art. Such carriers enable the preparation to be formulated as a tablet, pill, dragee, capsule, liquid, gel, syrup, slurry, suspension, and the like. Suitable excipients may also include, for example, fillers and cellulose preparations. Other excipients can include, for example, flavoring agents, coloring agents, detackifiers, thickeners, and other acceptable additives, adjuvants, or binders.

In various embodiments, the composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the compositions of this invention. Suitable biodegradable microspheres are shown, for example, in U.S. Pat. Nos. 4,897,268, 5,075,109, 5,928,647, 5,811,128, 5,820,883, 5,853,763, 5,814,344 and 5,942,252. "Compounds" as used herein, include the peptides, amino acid sequences, cargo compounds and complexes, and nucleic acids of the present invention.

Intravenous fluids for use in preparing pharmaceutical compositions to administer the Neisseria/AAEAP (SEQ ID NO: 25) transit peptides, cargos and transit peptide-cargo complexes and nucleic acids may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 4.

TABLE 4

Composition of Common Crystalloid Solutions

| Solution | Other Name | [$Na^+$] | [$Cl^-$] | [Glucose] |
|---|---|---|---|---|
| D5W | 5% Dextrose | 0 | 0 | 252 |
| 2/3 & 1/3 | 3.3% Dextrose/ 0.3 saline | 51 | 51 | 168 |
| Half-normal saline | 0.45% NaCl | 77 | 77 | 0 |
| Normal saline | 0.9% NaCl | 154 | 154 | 0 |

TABLE 4-continued

Composition of Common Crystalloid Solutions

| Solution | Other Name | [Na⁺] | [Cl⁻] | [Glucose] |
|---|---|---|---|---|
| Ringer's lactate* | Ringer's solution | 130 | 109 | 0 |

*Ringer's lactate also has 28 mmol/L lactate, 4 mmol/L K⁺ and 3 mmol/L Ca²⁺.

The half-life in the bloodstream of the compositions of the invention can be extended or optimized by several methods well known to those in the art, including but not limited to, circularized peptides (Monk et al., BioDrugs 19(4):261-78, (2005); DeFreest et al., J. Pept. Res. 63(5):409-19 (2004)), D,L-peptides (diastereomer), (Futaki et al., J. Biol. Chem. February 23; 276(8):5836-40 (2001); Papo et al., Cancer Res. 64(16):5779-86 (2004); Miller et al., Biochem. Pharmacol. 36(1):169-76, (1987)); peptides containing unusual amino acids (Lee et al., J. Pept. Res. 63(2):69-84 (2004)), and N- and C-terminal modifications (Labrie et al., Clin. Invest. Med. 13(5):275-8, (1990)). Of particular interest are d-isomerization (substitution) and modification of peptide stability via D-substitution or L-amino acid substitution.

When administration is by injection, composition may be formulated in aqueous solutions, preferably in physiologically compatible buffers such as Hanks solution, Ringer's solution, or physiological saline buffer. The solution may contain formulatory agents such as suspending, stabilizing and/or dispersing agents. Alternatively, the composition may be in powder form for constitution with a suitable vehicle, e.g., sterile pyrogen-free water, before use.

When administration is by inhalation, the composition may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch.

When administration is by topical administration, the composition may be formulated as solutions, gels, ointments, creams, suspensions, and the like, as are well known in the art. In some embodiments, administration is by means of a transdermal patch. When administration is by suppository (e.g., rectal or vaginal), composition may also be formulated in compositions containing conventional suppository bases.

When administration is oral, the composition can be readily formulated in combination with pharmaceutically acceptable carriers well known in the art. A solid carrier, such as mannitol, lactose, magnesium stearate, and the like may be employed; such carriers enable the chemotaxin to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include the composition allow for the release of the composition over extended periods of time, such that without the sustained release formulation, composition would be cleared from a subject's system, and/or degraded by, for example, proteases and simple hydrolysis before eliciting or enhancing an therapeutic effect.

Kits Comprising a Neisseria/AAEAP (SEQ ID NO: 25) Transit Domain

In another aspect, the invention provides kits containing one or more of the following in a package or container: (1) a reagent comprising a complex of a Neisseria or AAEAP (SEQ ID NO: 25) transit peptide linked to a cargo compound; (2) a reagent containing a pharmaceutically acceptable adjuvant or excipient; (3) a vehicle for administration, such as a syringe; (4) instructions for administration. Embodiments in which two or more of components (1)-(4) are found in the same container are also contemplated. In other embodiments, the kit components may include a reagent comprising a Neisseria or AAEAP (SEQ ID NO: 25) transit peptide, and a separate reagent comprising the cargo compound. In other embodiments, the kit comprises a reagent comprising the a Neisseria or AAEAP (SEQ ID NO: 25) transit peptide, but not a reagent comprising the cargo compound. In other embodiments, the reagents are formulated for intravenous administration, and/or the vehicle of administration is appropriate for intravenous administration. In some embodiments, the kit may comprise a cupredoxin-derived transit peptide, specifically Pseudomonas aeruginosa azurin. In other embodiments, the kits may comprise reagents for linking a cargo compound to a Neisseria/AAEAP transit peptide, or cupredoxin-derived transport peptide.

When a kit is supplied, the different components of the composition may be packaged in separate containers and admixed immediately before use. Such packaging of the components separately may permit long-term storage without losing the active components' functions.

The reagents included in the kit can be supplied in containers of any sort such that the life of the different components are preserved and are not adsorbed or altered by the materials of the container. For example, sealed glass ampules may contain lyophilized polypeptide or polynucleotide, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device, etc. Detailed instructions may not be physically associated with the kit; instead, a user may be directed to an internet web site specified by the manufacturer or distributor of the kit, or supplied as electronic mail.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended embodiments.

EXAMPLES

Example 1

Cloning And Expression of the Laz and H.8-Azurin Fusion Genes

Figure 1:
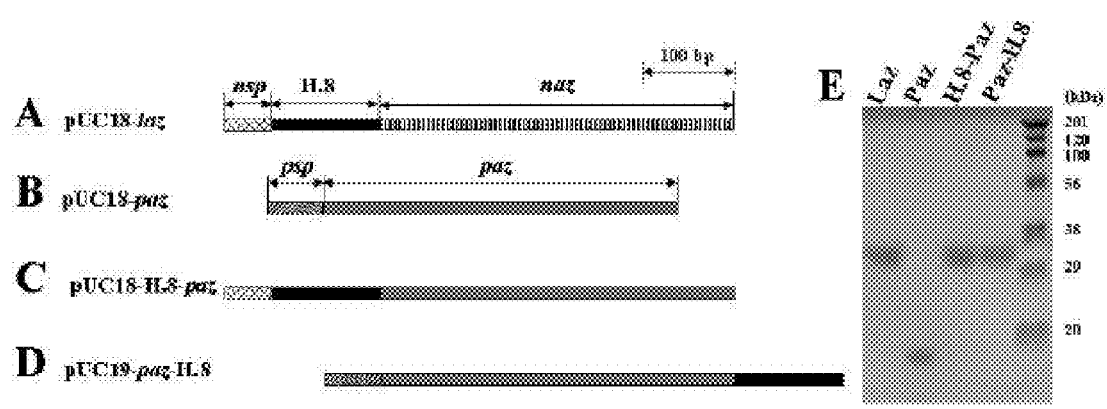
FIG. 1 depicts a schematic representation of laz from *Neisseria gonorrhoeae* (A) and paz from *Pseudomonas aeruginosa* (B). The *P. aeruginosa* azurin gene for cloning and hyperexpression in *E. coli* consisted of the azurin gene itself (paz) and the signal peptide (psp) sequence that determines its periplasmic location (B). The H.8 region of laz was cloned in frame either in the 5'-end of the paz gene (C) including the *Neisserial* signal sequence nsp (pUC18-H.8-paz) or at the 3'-end of the paz gene (D) (pUC19-paz-H.8). The detailed procedures for preparing the constructs are given in Example 1. naz, azurin-like sequence of *Neisseria gonorrhoeae* present in the laz gene; nsp, *Neisseria* signal peptide sequence. The signal peptide sequence in both cases is cleaved off to produce the mature Paz (periplasmic) and Laz (surface-exposed) proteins. (E), SDS-PAGE of Laz, Paz and the fusion proteins. The anomalous migration of the H.8 fusion proteins such as Laz, H.8-Paz or Paz-H.8 (all about 17 kDa) has previously been noted for lapidated H.8-containing proteins (Cannon, Clin. Microbiol. Rev. 2:S1-S4 (1989); Fisette, et al., J. Biol. Chem. 278:46252-46260 (2003)).

The laz gene from *Neisseria gonorrhoeae* was cloned (FIG. 1A) based on its known sequence (SEQ ID NO: 1). The *P. aeruginosa* azurin gene (SEQ ID NO: 2), termed paz (FIG. 1B), and the sequence of the H.8 epitope of laz from *N. gonnerrhoeae* (SEQ ID NO: 3), were used to clone in frame the H.8 epitope gene in the 5'-end of paz to produce H.8-paz (FIG. 1C) or in the 3'-end of paz to generate paz-H.8 (FIG. 1D), as described below.

Cell Lines and Reagents. Human cancer cells, bacterial strains and plasmids are listed in Table 5. The human breast cancer MCF-7 cells and brain tumor LN-229 cells are from the stock culture collection of the Department of Surgical Oncology, University of Illinois at Chicago (UIC). The cells were cultured in MEM with Eagle's salt containing 2 mM L-glutamine, 0.1 mM MEM essential amino acids and supplemented with 10% heat-inactivated fetal bovine serum, 100 units/ml penicillin and 100 μg/ml streptomycin. All cells were grown at 37° C. in 5% $CO_2$. (Yamada, et al., Proc. Natl. Acad. Sci. USA 99:14098-14103 (2002); Punj, et al., Oncogene 23:2367-2378 (2004)).

TABLE 5

Cancer cells, bacterial strains and genetic constructs

| Cells/strains/ plasmids | Relevant characteristics* | Reference |
|---|---|---|
| LN-229 | Human brain glioblastoma | Ishii, et al., Brain Pathol. 9:469-479 (1999) |
| MCF-7 | Human breast adenocarcinoma | Soule, et al., J. Natl. Cancer. Inst. 51:1409-1416 (1973); Punj, et al., Oncogene 23:2367-2378 (2004) |
| P. aeruginosa PAO1 | Prototroph, FP– (sex factor minus) | Holloway, et al., Microbiol. Rev. 43:73-102 (1979) |
| E. coli JM109 | Cloning and azurin expression strain | Yanisch-Perron, et al., Gene 33:103-119 (1985) |
| E. coli BL21 (DE3) | GST expression strain | Novagen |
| N. gonorrhoeae F62 | Prototroph used for DNA isolation | American Type Culture Collection |
| pUC18 | General cloning vector, $Ap^r$ | Yanisch-Perron, et al., id. |
| pUC19 | General cloning vector, $Ap^r$ | Yanisch-Perron, et al., id. |
| pUC18-laz | A 1 kb PCR fragment from genomic DNA of *N. gonorrhoeae* F62 cloned into pUC18 | Herein |
| pUC19-paz | A 0.55 kb PCR fragment from *P. aeruginosa* PAO1 cloned into HindIII and PstI digested | Yamada, et al., Proc. Natl. Acad. Sci. USA 99:14098-14103 (2002); Yamada, et al., Proc. Natl. Acad. Sci. USA 101:4770-775 (2004) |
| pUC18-H.8-paz | Fusion plasmid encoding H.8 from *N. gonorrhoeae* and azurin from *P. aeruginosa* PAO1, $Ap^r$ | Herein |
| pUC19-paz-H.8 | Fusion plasmid encoding azurin from *P. aeruginosa* PAO1 and H.8 from *N. gonorrhoeae*, $Ap^r$ | Herein |
| pGEX-5X-3 | GST gene fusion vectors, $Ap^r$ | Amersham |
| pET29a | *E. coli* expression vector, $Km^r$ | Novagen |
| pET29a-gst | pET29a derivative containing the gst gene, $Km^r$ | Herein |
| pET29a-H.8-gst | pET29a derivative containing H.8-gst gene, $Km^r$ | Herein |
| pGEX-5X-3-H.8 | pGEX-5X-3 derivative containing H.8-encoding region, $Ap^r$ | Herein |
| pET29a-gst-H.8 | pET29a derivative containing gst-H.8 gene, $Km^r$ | Herein |

*Ap, ampicillin; Km, kanamycin; GST, Glutathione S-transferase.

Cloning and Expression of the Paz and Laz Genes. The cloning and hyperexpression of the azurin gene has been described. (Yamada, et al., Proc. Natl. Acad. Sci. USA 99:14098-14103 (2002); Punj, et al., Oncogene 23:2367-2378 (2004)) The Laz-encoding gene (laz) of *Neisseria gonorrhoeae* was amplified by PCR with genomic DNA of *N. gonorrhoeae* strain F62 as template DNA. The forward and reverse primers used were 5'-CCG GAATTCCGGCAGGGATGTTGTAAATATCCG-3' (SEQ ID NO: 4) and 5'-GG GGTACCGCCGTGGCAGGCATACAGCATTTC AATCGG-3' (SEQ ID NO: 5) where the additionally introduced restriction sites of EcoRI and KpnI sites are underlined respectively. The amplified DNA fragment of 1.0 kb, digested with EcoRI and KpnI, was inserted into the corresponding sites of pUC18 vector (Yanisch-Perron, et al., Gene 33:103-119 (1985)) so that the laz gene was placed downstream of the lac promoter to yield an expression plasmid pUC18-laz (Table 5, FIG. 1).

The plasmids expressing fusion H.8 of *N. gonorrhoeae* Laz and azurin of *P. aeruginosa* (Paz) were constructed by PCR with pUC19-paz and pUC18-laz as templates. For H.8-Paz fusion, a 3.1 kb fragment was amplified with pUC18-laz as a template and primers, 5'-(Phosphorylated)GGCAG-CAGGGGCTTCGGCAGCATCTGC-3' (SEQ ID NO: 6) and 5'-CTGCAGGTCGACTCTAGAGGATCCCG-3' (SEQ ID NO: 7) where a SalI site is underlined. A PCR amplified a 0.4 kb fragment was obtained from pUC19-paz as a template and primers, 5'-(phosphorylated)GCCGAGTGCTCGGTGGA-CATCCAGG-3' (SEQ ID NO: 8) and 5'-TA CTCGAGTCACTTCAGGGTCAGGGTG-3' (SEQ ID NO: 9) where a XhoI site is underlined. A SalI digested PCR fragment from pUC18-laz and XhoI digested PCR fragment from pUC19-paz were cloned to yield an expression plasmid pUC18-H.8-laz (Table 5, FIG. 1).

For Paz-H.8 fusion, a 3.3 kb fragment was amplified with pUC19-paz as a template and primers, 5'-CTTCAGGGT-CAGGGTGCCCTTCATC-3' (SEQ ID NO: 10) and 5'-CTG-CAGGTCGACTCTAGAGGATCCCG-3' (SEQ ID NO: 11) where a BamHI site is underlined. A 0.13 kb fragment was amplified with pUC18-laz as a template and primers, 5'-(phosphorylated)TGCTCTCAAGAACCTGCCGCGC- CTGC-3' (SEQ ID NO: 12) and 5'-TAGGATCCTTAGGCAGCAGGGGCTTCGGCAGCATCTGC-3' (SEQ ID NO: 13) where a BamHI site is underlined and the additionally introduced TTA, corresponding to the bacterial gene stop codon, is italicized. Two BamHI digested PCR fragments were cloned to yield an expression plasmid pUC19-paz-H.8 (Table 5).

E. coli JM109 was used as a host strain for expression of azurin and its derivative genes. Recombinant E. coli strains were cultivated in 2×YT medium containing 100 µg/ml ampicillin, 0.1 mM IPTG and 0.5 mM $CuSO_4$ for 16 h at 37° C. to produce the azurin proteins.

Plasmid Construction for Fusion GST Proteins. The glutathione S-transferase (GST)-encoding gene was amplified by PCR with pGEX-5X-3 (GE Healthcare Bio-Sciences Corp., Piscataway, N.J.) as template DNA. The forward and reverse primers used were 5'-CGAGCTCATGTCCCCTATACTAGGTTATTGG-3' (SEQ ID NO: 14) and 5'-CCCAAGCTTTCAGGGGATCCCACGACCTTCGATCAGATCC-3' (SEQ ID NO: 15) where the additionally introduced restriction sites of SacI and HindIII are underlined and the additionally introduced TCA, corresponding bacterial gene stop codon, is italicized respectively. The amplified DNA fragment of 1.0 kb, digested with SacI and HindIII, was inserted into the corresponding sites of pET29a vector to yield an expression plasmid pET29a-gst (Table 5).

For H.8-GST fusion, the signal peptide and H.8-encoding region of laz was amplified by PCR with pUC18-laz as template DNA. The forward and reverse primers used were 5'-GGAATTCATATGAAAGCTTATCTGGC-3' (SEQ ID NO: 16) and 5'-CCGGAATTCGGCAGCAGG GGCTTCGGC-3' (SEQ ID NO: 17) where the additionally introduced restriction sites of NdeI and EcoRI sites are underlined respectively. The amplified DNA fragment of 0.14 kb, digested with NdeI and EcoRI, was inserted into the corresponding sites of pET29a-gst vector to yield an expression plasmid pET29a-H.8-gst (Table 5).

For GST-H.8 fusion, the H.8-encoding region was amplified by PCR with pUC18-laz as template DNA. The forward and reverse primers used were 5'-CGGGATCCCCTGCTCTCAAGAACCTGCCGCGCC-3' (SEQ ID NO: 18) and 5'-CGGAATTCTTAGGCAGCAGGGGCTTCGGCAGCATCTGCAGG-3' (SEQ ID NO: 19) where the additionally introduced restriction sites of BamHI and EcoRI are underlined and the introduced bacterial gene stop codon TTA is italicized. The amplified DNA fragment of 0.14 kb, digested with BamHI and EcoRI, was inserted into the corresponding sites of pGEX-5X-3 vector to yield a pGEX-5X-3-H.8. The GST-H.8 fusion region was then amplified by PCR with pGEX-5X-3-H.8 as a template DNA. The forward and reverse primers used were 5'-CGAGCTCATGTCCCCTATACTAGGTTATTGG-3' (SEQ ID NO: 20) and 5'-CCGCTCGAGTCAGGCAGCAGGGGCTTCGGCAG-3' (SEQ ID NO: 21) where the additionally introduced restriction sites of SacI and XhoI sites are underlined and the bacterial gene stop codon TCA is italicized. The amplified DNA fragment of 1.1 kb, digested with SacI and XhoI, was inserted into the corresponding sites of pET29a vector to yield an expression plasmid pET29a-gst-H.8 (Table 5).

E. coli BL21 (DE3) was used as a host strain for expression of the gst and its fusions derivatives.

When E. coli strains harboring these plasmids were grown in presence of IPTG, cells lysed and the proteins purified as described for azurin (Yamada, et al., Proc. Natl. Acad. Sci. USA 99:14098-14103 (2002); Punj, et al., Oncogene 23:2367-2378 (2004); Yamada, et al., Cell. Microbiol. 7:1418-1431 (2005)), the various azurin derivatives migrated on SDS-PAGE as single components (FIG. 1E), although the H.8 containing proteins (about 17 kDa) showed anomalous migrations, as noted before (Cannon et al., id.; Fisette et al., id.).

Example 2

H.8 Enhances the Cytotoxicity of P. aeruginosa Azurin Towards Glioblastoma Cells but not Breast Cancer Cells The preferential entry of Paz towards cancer cells (Yamada, et al., Cell. Microbiol. 7:1418-1431 (2005)) and its cytotoxicity, both in vitro and in vivo towards human melanoma (Yamada, et al., Proc. Natl. Acad. Sci. USA 99:14098-14103 (2002)) and breast cancer (Punj, et al., Oncogene 23:2367-2378 (2004)), have been reported. However, no effect of Paz or Laz towards brain tumors such as glioblastomas is known. Here the effect of Paz, Laz, H.8-Paz (H.8 epitope in the N-terminal of Paz) and Paz-H.8 (H.8 epitope in the C-terminal of Paz) on both glioblastoma (LN-229 cell line) and breast cancer (MCF-7 cell line) cells was studied.

Preparations of Proteins. Azurin (Paz) of P. aeruginosa, Laz of N. gonorrhoeae, Paz-H.8 and H.8-Paz were purified as described previously. (Yamada, et al., Proc. Natl. Acad. Sci. USA 99:14098-14103 (2002); Punj, et al., Oncogene 23:2367-2378 (2004); Yamada, et al., Cell. Microbiol. 7:1418-1431 (2005)) All recombinant GST fusion derivatives were purified as described before. (Yamada, et al., Cell. Microbiol. 7:1418-1431 (2005)) A chemically-synthesized 39-amino acid H.8 peptide was purchased.

Cytotoxicity Assay. The 3-(4,5-dimethylthiazol-2-yl-2,5-diphenyl) tetrazolium bromide (MTT) assay was performed to determine the cytotoxicity toward cancer cells. Cells ($5 \times 10^3$ per well) were seeded into 96-well culture plates in 100:1 of the medium at 37° C. with 5% $CO_2$. After overnight incubation, the supernatant was removed and fresh media containing proteins at various concentrations as specified were added to the attached cells. These cells were incubated for various time periods as specified before the number of live cells was determined by MTT assay by adding 10 µl of 5 mg/ml MTT (Sigma-Aldrich, St. Louis Mo.) solution to the culture and incubating for 2 h at 37° C. MTT reaction was terminated by adding 100 µl of 40 mM HCl in isopropanol. The MTT formazan formed was measured spectrophotometrically according to the method described by Mosmann (J. Immunol. Methods 65:55-63 (1983)).

Figure 2:
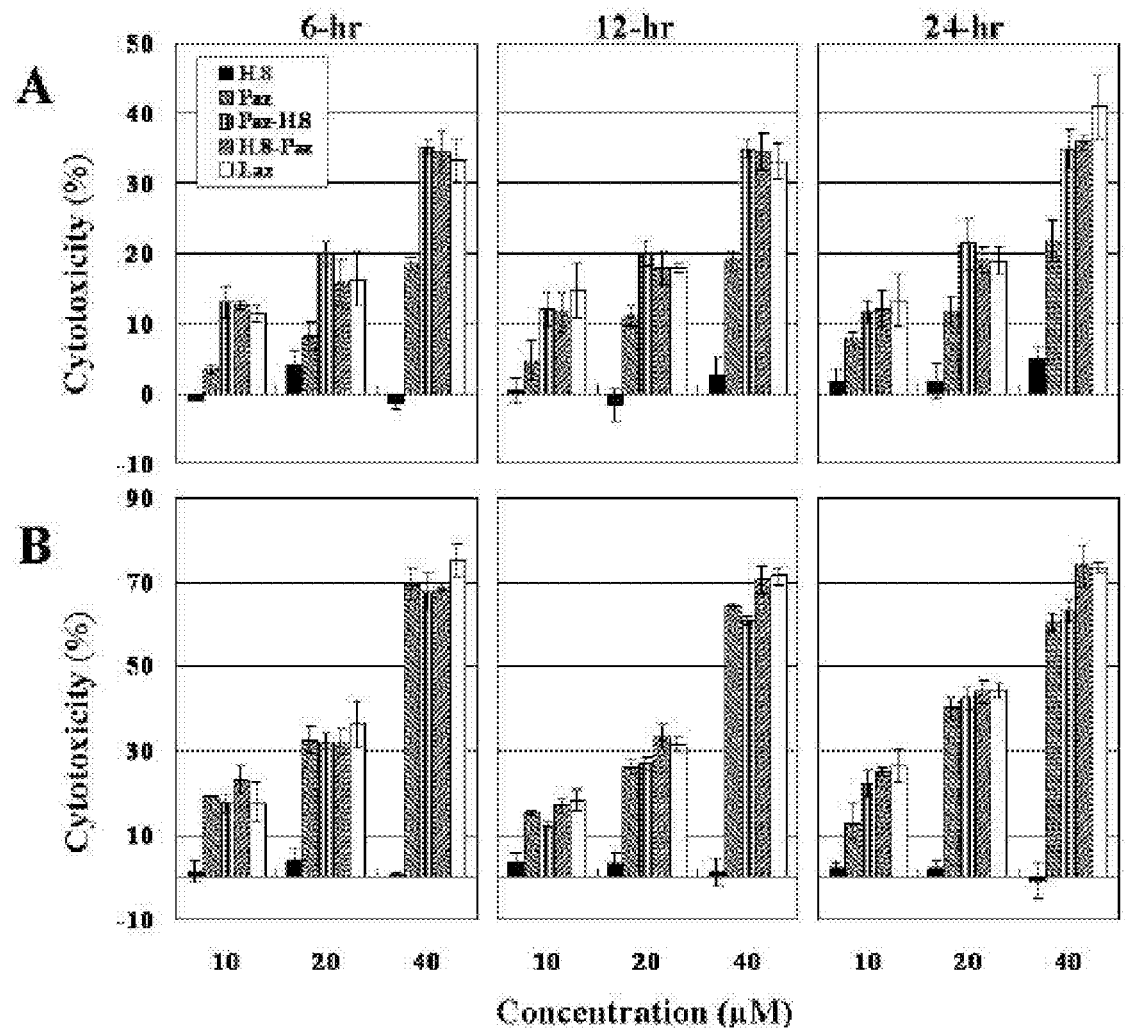
FIG. 2 depicts graphs illustrating the degree to which the H.8-Paz fusion proteins are cytotoxic to various cancer cells.

The synthetic H.8 peptide had very little cytotoxicity towards either glioblastoma LN-229 (FIG. 2A) or breast cancer MCF-7 (FIG. 2B) cells. The effect of azurin (Paz) was dose dependent, albeit low, in glioblastoma (FIG. 2A) but not in breast cancer (FIG. 2B) cells with increasing cytotoxicity as the azurin concentration was raised from 10 µM to 40 µM. The cytotoxicity increased only marginally beyond a 6 h incubation period. Most notable was the difference in the cytotoxicity of Paz, Paz-H.8, H.8-Paz and Laz in glioblastoma and breast cancer cells. While Paz, Paz-H.8, H.8-Paz and Laz had essentially identical cytotoxicities at all doses in MCF-7 cells for different periods of incubation (FIG. 2B), Paz had much lower cytotoxicity than Paz-H.8, H.8-Paz or Laz for glioblastoma cells, particularly at shorter periods of incubation (6 h). Thus the H.8 moiety, while itself lacking cytotoxicity, appeared to enhance the cytotoxicity of Paz, but only towards glioblastoma and not towards breast cancer cells.

Example 3

H.8 Epitope Present in Paz or Laz Facilitates the Uptake of Azurin in Glioblastoma Cells The enhanced cytotoxicity of Paz-H.8, H.8-Paz and Laz towards glioblastoma cells as compared to Paz, raised the question if the H.8 moiety somehow facilitated the uptake of azurin in glioblastoma cells. Alexa Fluor® 568-labeled red fluorescent proteins (Invitrogen-Molecular Probes Corp., Carlsbad Calif.) were used to determine the internalization of these proteins inside glioblastoma and breast cancer cells. This technique was previously used to demonstrate the internalization of azurin in MCF-7 cells (Punj, et al., Oncogene 23:2367-2378 (2004); Yamada, et al., Cell. Microbiol. 7:1418-1431 (2005)).

Confocal Microscopy. For preparation of microscopic samples, cells were cultured on coverslips overnight at 37° C. under 5% $CO_2$. Pre-warmed 37° C. fresh media were mixed with red fluorescent-labeled (Alexa Fluor® 568) azurin or GST fusion derivatives, and incubated with the cells for indicated times. The cells were washed with PBS, and fixed with methanol at −20° C. for 5 min. After washing with PBS thrice and the addition of mounting media containing 1.5 mg/ml 4,6-diamidino-2-phenylindole (DAPI) for staining nuclei (VECTASHIELD®, Vector Laboratories, Burlingame Calif.), images were taken by using a Carl Zeiss LSM510 laser scanning confocal microscope. (Yamada, et al., Cell. Microbiol. 7:1418-1431 (2005))

Azurin (Paz) was internalized with a reduced efficiency than Paz-H.8, H.8-Paz and Laz, demonstrating a barrier for Paz entry in glioblastoma LN-229 cells (FIGS. 3A and 4A). In contrast, Paz was efficiently internalized in breast cancer MCF-7 cells as previously reported, with an equal or somewhat higher efficiency than Paz-H.8, H.8-Paz or Laz (FIGS. 3B and 4B). (Punj, et al., Oncogene 23:2367-2378 (2004); Yamada, et al., Cell. Microbiol. 7:1418-1431 (2005)) A dose dependency of Laz entry in LN-229 cells demonstrated an optimum concentration of about 16 μM during a 30 min incubation period at 37° C. (FIGS. 3C and 4C) beyond which there was no further enhancement (data not shown). At 10 μM concentration, while the bulk of Laz was internalized in LN-229 cells in about 10 to 20 min (FIGS. 3D and 4D), the internalization of Paz was minimal under such conditions (FIG. 3E), suggesting that Paz internalization was inherently inefficient in LN-229 cells. The significant internalization of Paz-H.8 and H.8-Paz, similar to Laz but in contrast to Paz in LN-229 cells (FIGS. 3A and 4A) appeared to suggest that the relative location of the H.8 moiety, either in the N-terminal or in the C-terminal of Paz, did not affect its ability to promote internalization of the Paz moiety in glioblastoma cells.

Example 4

H.8 Moiety Promotes Paz Entry in Glioblastoma but not in Breast Cancer Cells

In order to determine if the H.8 epitope need to be a part of Paz, as in Laz, or could it function alone to promote Paz entry into glioblastoma cells, various H.8 fusion proteins, in addition to H.8 alone where used. Since small peptides such as the 39-amino acid synthetic H.8 moiety have low stability in solution, we constructed glutathione S-transferase (GST) fusions with the H.8 moiety, similar to Paz-H.8 or H.8-Paz, such that H.8 was incorporated in the N-terminal of GST (H.8-GST) or in the C-terminal of GST (GST-H.8). The construction of the GST fusion peptides is described under Example 1.

Alexa Fluor® 568-conjugated Paz, fluorescing red, was incubated with unlabeled synthetic H.8 peptide, GST, GST-H.8 and H.8-GST fusion proteins separately, along with phosphate-buffered saline (PBS) as a control, and determined the internalization of 20 μM Paz mixture in LN-229 cells after incubation at 37° C. for 30 min. The synthetic H.8 peptide, when introduced separately along with Paz, did enhance Paz internalization (FIG. 5A) as compared to PBS (FIG. 5E), GST (FIG. 5B) or GST-H.8 (FIG. 5C). Quantification of the fluorescence showed that the H.8 peptide stimulated Paz entry by 2.1 fold. The presence of H.8-GST, however, significantly enhanced (more than 3 fold) the internalization of Paz (FIG. 5D). GST-H.8, on the other hand, showed only a mild stimulation (FIG. 5C). Paz itself entered only slowly (FIG. 5E) in glioblastoma cells, demonstrating that the entry in the brain tumor cells is mediated by H.8. H.8 alone did not enter the glioblastoma cells (FIG. 3A) but its ability to stimulate the internalization of Paz (FIG. 5A) reflects its ability to facilitate entry of proteins into brain tumor cells.

Example 5

Enhanced Internalization of Paz in Presence of H.8-GST in Glioblastoma Cells Lead to Higher Cytotoxicity in such Cells We incubated the synthetic H.8 peptide, GST, GST-H.8 and H.8-GST proteins (20 μM each) in absence or in presence of 20 μM Paz with LN-229 cells for 24 h and then measured the extent of cytotoxicity by measuring the viable glioblastoma cells by the MTT assay after 24 h. In absence of Paz, none of the H.8 peptide, GST or GST fusion proteins demonstrated any significant cytotoxicity (FIG. 5F,—Paz). In presence of 20 μM Paz, which itself demonstrated a low cytotoxicity in presence of the H.8 peptide or the PBS (FIG. 5F, +Paz), considerable enhancement of cytotoxicity was observed only in presence of the H.8-GST (FIG. 5F, +Paz), although GST itself or GST-H.8 did show some enhancement of cytotoxicity (FIG. 5F, +Paz). Taken together, these data suggest that the H.8 moiety, when present as part of or in presence of a protein such as Paz, facilitates the transport of Paz inside such cells, resulting in enhanced cytotoxicity.

Example 6

H.8 Mediate Crossing of the BBB to Allow Entry in Brain

The ability of the H.8 epitope to allow enhanced internalization of a fusion or individual protein in glioblastoma LN-229 cells (FIGS. 3A, 4A and 5D) raised the question of whether H.8 as part of the N-terminal of H.8-Paz or Laz promoted crossing of the BBB and allow transport of these proteins from peripheral circulation to brain venules.

Odyssey® Assay. All proteins were labeled using IRDye® 800CW (LI-COR Biosciences, Lincoln, Nebr.) under conditions recommended by the manufacturers. Five hundred μg of Paz, H.8-Paz and Laz conjugated with IRdye® 800CW were injected intraperitoneally in nude mice. After 24 h, the mice were sacrificed, brains were taken out and brain images were detected with the LI-COR Odyssey® Infrared Imaging System (84 μm resolution, 1 mm offset). The mice brains were then cut horizontally and rostral mesencephalon region images were taken for detecting the presence of the labeled proteins.

Quantification of Fluorescence in Azurin Proteins. Quantification of fluorescence was measured by using Adobe® Photoshop® as follows: one cell was selected by Lasso Tool of Photoshop®, and the mean value was taken from red histogram of image menu. At least three different cells were measured for one sample and the standard deviation was calculated.

Five hundred μg of Paz, H.8-Paz and Laz proteins, labeled with the infrared dye IRdye® 800 CW (LI-COR Bioscience), was injected intraperitoneally into live nude mice. After 24 h, the mice were sacrificed, the brains were isolated and images were taken, using the LI-COR Odyssey® Infrared Imaging system. While Paz was found to enter the brain venules in small amounts, much more Laz and in particular H.8-Paz (more than 4 fold) was detected inside the brain under such conditions (FIG. 6), demonstrating a clear role of the H.8 epitope to allow entry of the fusion proteins into the brain.

Example 7

The H.8 Epitope, when Present in the N-Terminal, Allows Bacterial Surface Display of the Periplasmic Proteins To investigate if the N-terminal localization of the H.8 epitope in Laz contributes to its surface display, H.8 fusion derivatives were constructed in the N- and C-terminals of GST (FIG. 5) and Paz (FIG. 2 and FIGS. 3A/B and 4A/B), as described in Example 1.

Localization of Surface-Exposed Proteins in *E. coli*. *E. coli* strain BL21 (DE3) harboring pET29a-gst, pET29a-H.8.gst or pET29a-gst-H.8 and *E. coli* strain JM109 harboring pUC19-paz, pUC19-paz-H.8, pUC18-H.8-paz or pUC18-laz were cultured at 37° C. with 0.4 mM Isopropyl β-D-thiogalactoside (IPTG). One ml each of these bacterial cultures was centrifuged and the resultant pellets were collected. After washing with PBS twice, one ml 1% FBS-PBS containing anti-GST antibody (1:2000) for GST derivatives or anti-azurin antibody (1:500) for azurin derivatives was added. Cell suspensions were incubated on ice for 1 h and then washed with PBS twice. FITC-conjugated anti-rabbit IgG for GST derivatives or FITC-conjugated anti-rabbit antibody for azurin derivatives was applied and incubated on ice for 30 min. To remove unbound antibody, cells were washed with PBS twice, and fixed with ethanol on ice. *E. coli* samples treated with DAPI were then observed under the confocal microscope.

The H.8 fusion proteins were purified (FIG. 1E and FIG. 7A). The cellular localizations of GST, as well as the two H.8 fusions in the N- and C-terminals (H.8-GST and GST-H.8) are shown in FIG. 7B. All three proteins were hyper-expressed in *E. coli* and present in the whole cell lysates of *E. coli*, when detected by Western blotting using anti-GST antibodies (FIG. 7B). When the periplasmic fractions were isolated from *E. coli* and the presence of the three proteins checked, GST and GST-H.8 proteins were detected in significant amounts (FIG. 7B, lanes 1 and 3 under periplasmic fraction) but only small amounts of the H.8-GST (FIG. 7B, lane 2 under periplasmic fraction) could be detected in such periplasmic fractions.

To examine if the rest of the H.8-GST fusion protein might have been transported to the surface of *E. coli* cells, cells hyperexpressing the three proteins were grown and harvested, washed, treated with anti-GST antibody to bind any surface-exposed GST, washed again and treated with FITC-conjugated secondary antibodies. If the GST is surface-exposed, anti-GST antibodies would bind to them which then could be detected by FITC-conjugated secondary antibodies. Indeed, only *E. coli* cells harboring H.8-GST showed the FITC generated green fluorescence (FIG. 7C, H.8-GST), suggesting that the presence of the H.8 epitope in the N-terminal of GST promoted its transport to the cell surface. The presence of the H.8 moiety in the C-terminal of GST (GST-H.8), as well as GST itself, remained largely periplasmic and intracellular without any surface display (FIG. 7C, GST and GST-H.8).

Using the same technique as described above, we determined that Paz and Paz-H.8 remained intracellular (FIG. 7D, Paz and Paz-H.8) while both H.8-Paz and Laz showed surface display, confirming that the presence of the H.8 in the N-terminal, perhaps requiring a free cysteine for lipidation, is important for transport of the fusion proteins through the outer membrane to reach the surface.

Example 8

Treatment of Patients Suffering from Cancer

A Phase I/II clinical trial of a H.8-Paz fusion (Study Drug) will be performed in patients suffering from cancer. Specifically, the H.8 domain from Laz-encoding gene (laz) of *Neisseria gonorrhoeae* and the cargo compound is the azurin from *Pseudomonas aeruginosa* (paz), making the fusion protein "H.8-paz." This fusion protein will be constructed as illustrated in Example 1.

Forty-nine adult patients with histologically verified cancers of the brain who demonstrate clinical and radiographic progression or recurrence following adequate treatment by currently available FDA-approved chemotherapeutic drugs and regimen will be enrolled in an open-label prospective study administering the Study Drug. To be eligible for enrollment in the study, all patients demonstrate increasing volume of measurable tumor after completion of approved course of chemotherapy regimens. The evidence of persistent metastatic deposits and/or continued increase in size or volume must be histologically established. This histological proof can be obtained by a fine needle aspiration (FNA) biopsy.

The treatment program will be instituted after obtaining informed consent from all patients in accordance with the Institutional Review Board of the University of Illinois, Chicago and the FDA. The patients will have no intercurrent illness such as other malignancy, history of previous malignancy, blood dyscrasias, insulin dependent diabetes or other serious cardiovascular diseases which might interfere in appropriate evaluation of the effects of the proposed therapy. Baseline blood work (Complete Blood Counts [CBC] and Serum Chemistry) including liver function studies (LFT) will be performed prior to initiation of therapy. All eligible patients must not receive any cancer chemotherapy concurrently during the period of the trial.

The study drug(s) will be administered by daily intravenous injection of a pharmaceutically acceptable preparation of the Study Drug for 12 weeks and the subjects will be observed for any dose limiting toxicity. There will be 7 dose levels starting with 10 mg/kg/day and increasing by 5 mg/kg/day up to a maximum dose of 50 mg/kg/day. The efficacy of each dose level will be recorded in 7 patients with advanced measurable cancer.

The response will be estimated by measuring the measurable tumor in 2 dimensions (a and b). 1) Total disappearance of the target tumors will be considered as complete response (CR); 2) A 75% reduction will be considered excellent, partial response (PR); and 3) A good response (PR) will be post treatment reduction in size by 50%. 4) Reduction of 25% in size will be considered as stable disease (SD) and 5) <25% will be considered as no response (NR). Patients demonstrating a progression of disease will have their treatment discontinued but will be followed for an additional 12 weeks.

Total disappearance, and any reduction in size of the target tumors will indicate that the H.8-azurin treatment is effective for treating cancer. Other indications that the H.8-azurin treatment is effective are a decrease rate of in the appearance of new brain tumors and a decrease in the angiogenesis associated with tumors.

Various modifications and variations of the described examples and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in related fields are intended to be within the scope of the following claims.

The invention claimed is:

1. A method of treating a patient with cancer, comprising administering to said patient a therapeutically effective amount of a complex comprising at least one cargo compound and an isolated transit peptide, wherein the isolated transit peptide is a truncation of Laz, Lip or Pan 1 from *Neisseria*, wherein the isolated transit peptide facilitates the entry of a linked molecule into a mammalian brain cancer cell or across the blood-brain barrier, and wherein the isolated transit peptide is linked to the at least one cargo compound.

2. The method of claim 1, wherein the complex is administered in a manner selected from the group consisting of intravenously, topically, subcutaneously, intramuscularly, and into tumor.

3. The method of claim 1, further comprising co-administering another cancer treatment.

4. A method for imaging cancer in a patient, comprising administering a complex comprising at least one cargo compound and an isolated transit peptide, wherein the isolated transit peptide is a truncation of Laz, Lip or Pan 1 from *Neisseria*, wherein the isolated transit peptide facilitates the entry of a linked molecule into a mammalian brain cancer cell or across the blood-brain barrier, wherein the isolated transit peptide is linked to the at least one cargo compound, and wherein the cargo compound is a detectable substance, and detecting the location of the cargo compound within said patient.

5. The method of claim 4, wherein the cargo compound is an X-ray contrast agent and the location of the cargo compound is detected by X-ray CT.

6. The method of claim 4, wherein the cargo compound is a magnetic resonance imaging contrast agent and the location of the cargo compound is detected by MRI.

7. The method of claim 4, wherein the cargo compound is an ultrasound contrast agent and the location of the cargo compound is detected by ultrasound imaging.

8. A method for diagnosing cancer, comprising contacting a cell with a complex comprising at least one cargo compound and an isolated transit peptide, wherein the isolated transit peptide is a truncation of Laz, Lip or Pan 1 from *Neisseria*, wherein the isolated transit peptide facilitates the entry of a linked molecule into a mammalian brain cancer cell or across the blood-brain barrier, wherein the isolated transit peptide is linked to the at least one cargo compound, and wherein the cargo compound is a detectable substance, and detecting the cellular location of the cargo molecule.

9. A method for treating or diagnosing a patient with a condition related to the brain, comprising co-administering to said patient an isolated transit peptide which is a truncation of Laz, Lip or Pan 1 from *Neisseria*, and which facilitates the entry of a linked molecule into a mammalian brain cancer cell or across the blood-brain barrier, and at least one cargo compound.

10. The method of claim 9, wherein a cupredoxin-derived transport peptide is additionally coadministered.

11. A method for treating or diagnosing a patient with a condition related to the brain, comprising co-administering to said patient a transit peptide comprising a region consisting of at least 4 imperfect or perfect repeats of Ala-Ala-Glu-Ala-Pro (SEQ ID NO: 25), and which has at least about 50% AAEAP (SEQ ID NO: 25) pentapeptide repeats per total length, and at least one cargo compound.

12. The method of claim 11, wherein a cupredoxin-derived transport peptide is additionally coadministered.

13. The method of claim 1, wherein the isolated transit peptide consists of SEQ ID NO: 24.

14. The method of claim 4, wherein the isolated transit peptide consists of SEQ ID NO: 24.

15. The method of claim 8, wherein the isolated transit peptide consists of SEQ ID NO: 24.

16. The method of claim 9, wherein the isolated transit peptide consists of SEQ ID NO: 24.

* * * * *